(12) United States Patent
Heroux et al.

(10) Patent No.: US 7,439,017 B2
(45) Date of Patent: Oct. 21, 2008

(54) ASSAYS FOR MEASURING NUCLEIC ACID BINDING PROTEINS AND ENZYME ACTIVITIES

(75) Inventors: Jeffrey A. Heroux, Middletown, MD (US); Maura C. Kibbey, Darnestown, MD (US); John H. Kenten, Boyds, MD (US)

(73) Assignee: BioVeris Corporation, Gaithersburg, MD (US)

( * ) Notice: Subject to any disclaimer, the term of this patent is extended or adjusted under 35 U.S.C. 154(b) by 261 days.

(21) Appl. No.: 09/976,437

(22) Filed: Oct. 15, 2001

(65) Prior Publication Data

US 2002/0146722 A1 Oct. 10, 2002

Related U.S. Application Data

(62) Division of application No. 09/157,808, filed on Sep. 17, 1998, now Pat. No. 6,312,896.

(51) Int. Cl.
*C07K 1/00* (2006.01)
*C12Q 1/68* (2006.01)

(52) U.S. Cl. .......................................... 435/6; 530/350

(58) Field of Classification Search ..................... 435/6; 536/24.32, 24.33, 23.1; 530/350
See application file for complete search history.

(56) References Cited

U.S. PATENT DOCUMENTS

| | | | |
|---|---|---|---|
| 5,157,032 A | 10/1992 | Barton | |
| 5,453,356 A | 9/1995 | Bard et al. | |
| 5,597,910 A | 1/1997 | Gudibande et al. | |
| 5,610,017 A | 3/1997 | Gudibande et al. | |
| 5,620,850 A | 4/1997 | Bamdad et al. | |
| 5,635,347 A | 6/1997 | Link et al. | |
| 5,714,089 A | 2/1998 | Bard et al. | |
| 5,779,976 A | 7/1998 | Leland et al. | |
| 5,834,285 A * | 11/1998 | Comb et al. | 435/194 |
| 5,866,434 A * | 2/1999 | Massey et al. | 436/526 |
| 6,048,687 A | 4/2000 | Kenten et al. | |
| 6,174,709 B1 | 1/2001 | Kenten et al. | |
| 6,207,369 B1 | 3/2001 | Wohlstadter et al. | |
| 6,569,619 B1 * | 5/2003 | Sivaraja | 435/6 |

FOREIGN PATENT DOCUMENTS

| | | | |
|---|---|---|---|
| EP | 0 570 518 B1 * | 5/1992 | |
| EP | 0 658 564 A1 | 6/1995 | |
| EP | 0 570518 B1 * | 11/1998 | |
| WO | WO 87/06706 | 11/1987 | |
| WO | WO 97/33176 | 9/1997 | |
| WO | WO 98/12539 | 3/1998 | |
| WO | WO 9812539 A1 * | 3/1998 | |

OTHER PUBLICATIONS

Shukla et al. An activity gel assay for the detection of DNA helicases and nucleases from cell-free extracts. Nucleic Acids Res., vol. 22, No. 9, pp. 1626-1631, 1994.*
Garner, Mark M., et al, *Nucleic Acids Research*, vol. 9, No. 13, pp. 3047-3060, 1981 A gel electrophoresis method for quantifying the binding of proteins to specific DNA regions: application to components of the *Escherichia coli* lactose operon regulatory system.
Galas, David J, et al, *Nucleic Acids Research*, vol. 5, No. 9, pp. 3157-3170, Sep. 1978, "DNAase footprinting: a simple method for the detection of protein-DNA binding specificity".
Wilkinson, K.F. et al, *Pharmaceutical Research*, vol. 10 No. 4, pp. 562-566 (1993), "Development of Activity Assays for High-Volume Evaluation . . . ".
Kenrick, M.K., *Nucleic Acids Research*, vol. 25, No. 14, pp. 2947-2948 (1997), "A homogeneous method to quantify mRNA . . . ".
Heroux et al, PCR methods and Applications, vol. 4, No. 6, pp. 327-330, 1995, "Quantitative Analysis of Specific mRNA . . . ".
Yacoub, A. et al, The EMBO Journal, 196, vol. 15, No. 9, pp. 2306-2312, "A drosophila ribosomal protein contains . . . ", (1996).
Skerra Phosphorothioate primers improve the amplification of DNA sequences by DNA polymerases with proofreading activity. Nucleic Acids Res. vol. 20, pp. 3351-3554 (1992).
Brenowitz et al, Dnase I footprint analysis of protein-DNA binding. In Current Protocols in Molecular Biology (Ausubel et al. Eds.) pp. 12.4.1-12.4.16 John Wiley & Sons, New York (1989).
DiCesare et al, A high-sensitivity electrochemiluminescence-based detection system for automated PCR product quantitation Biotechniques vol. 15, pp. 152-157, 1992.

* cited by examiner

*Primary Examiner*—Suryaprabha Chunduru
(74) *Attorney, Agent, or Firm*—Foley & Lardner LLP

(57) ABSTRACT

The present invention provides processes for measuring DNA or RNA binding proteins, specific nucleic acids, as well as enzyme activities using labeled nucleic acids of labeled protein/peptide molecules.

32 Claims, 8 Drawing Sheets

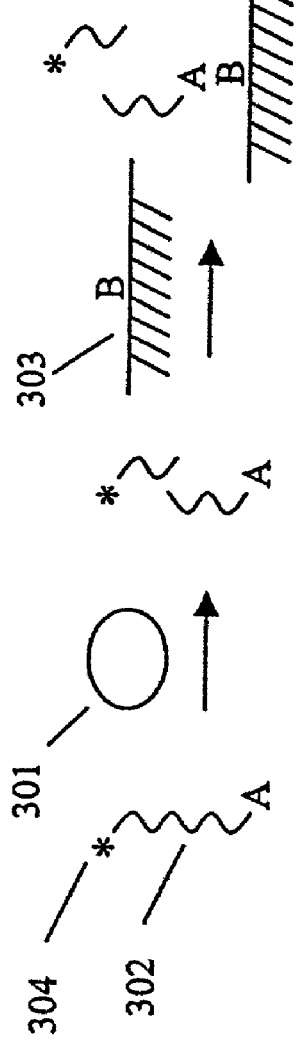
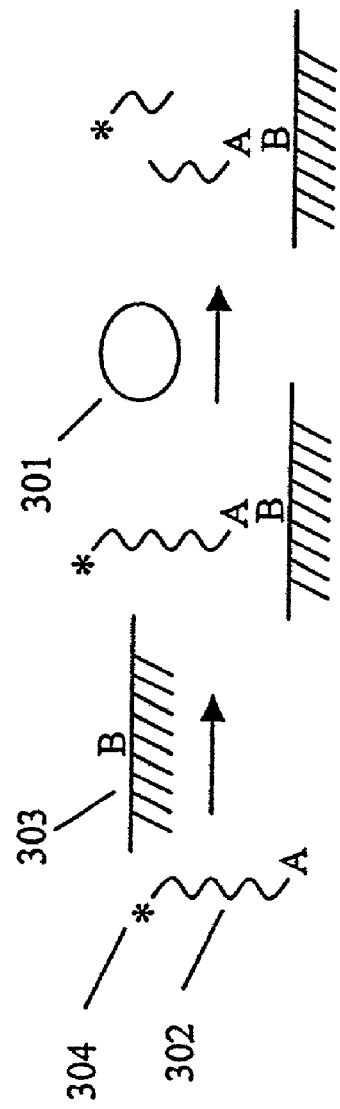
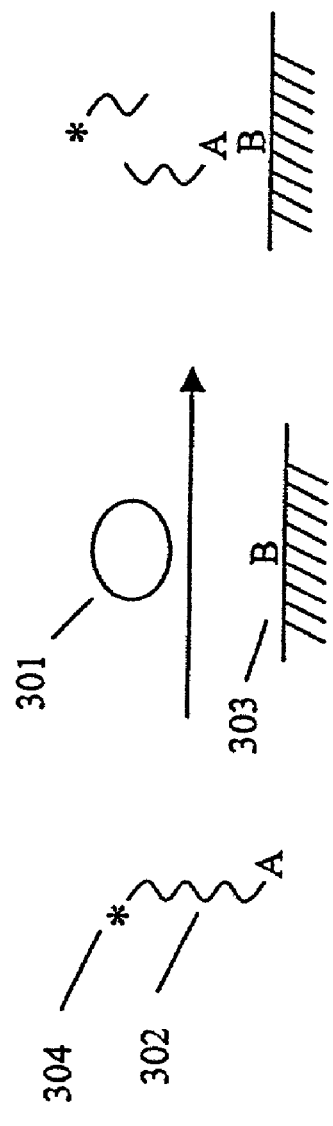
Fig. 3a
Fig. 3b
Fig. 3c

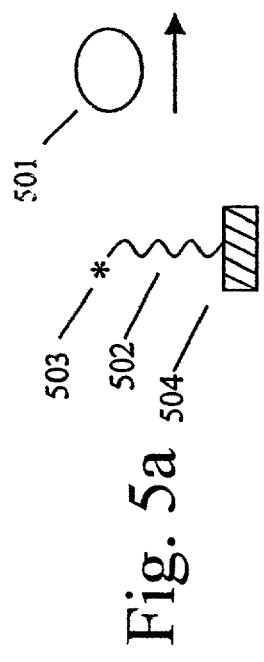
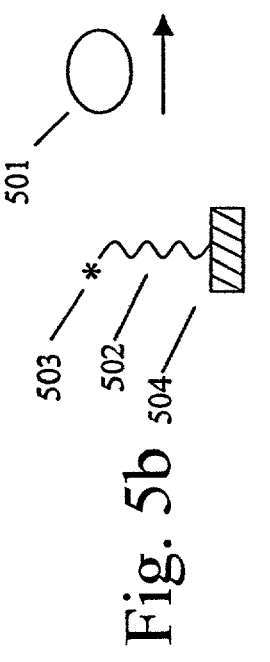
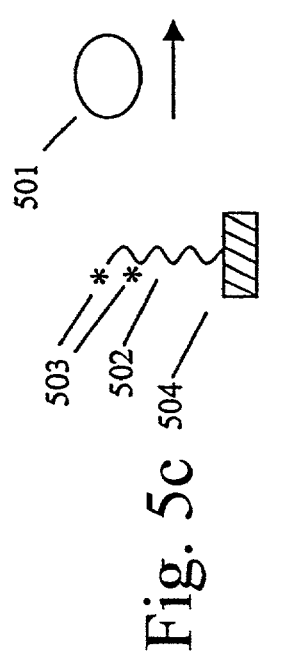
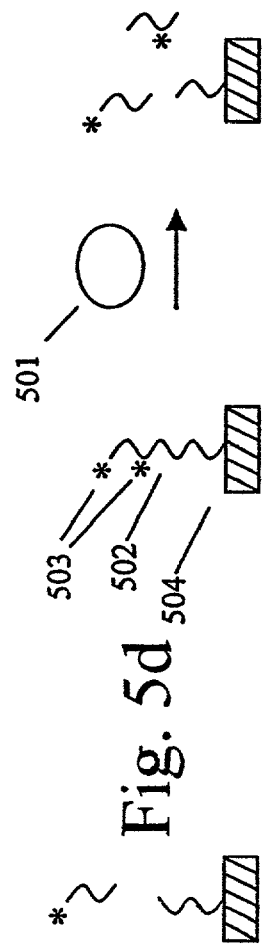
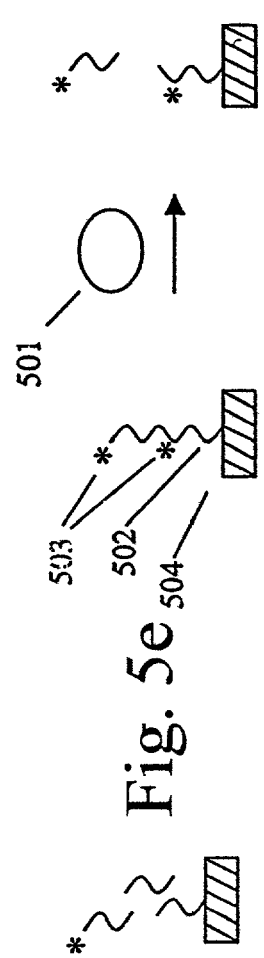
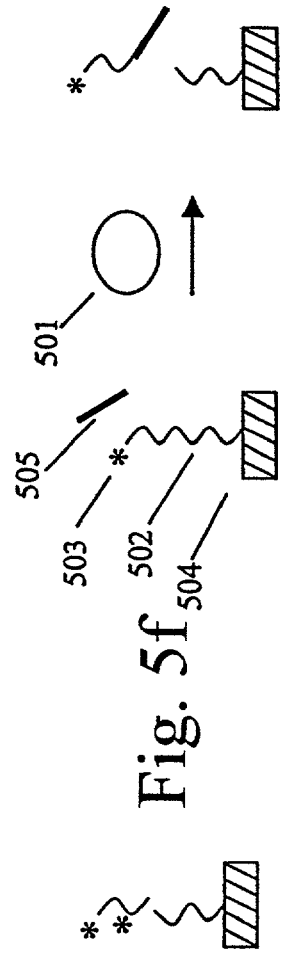

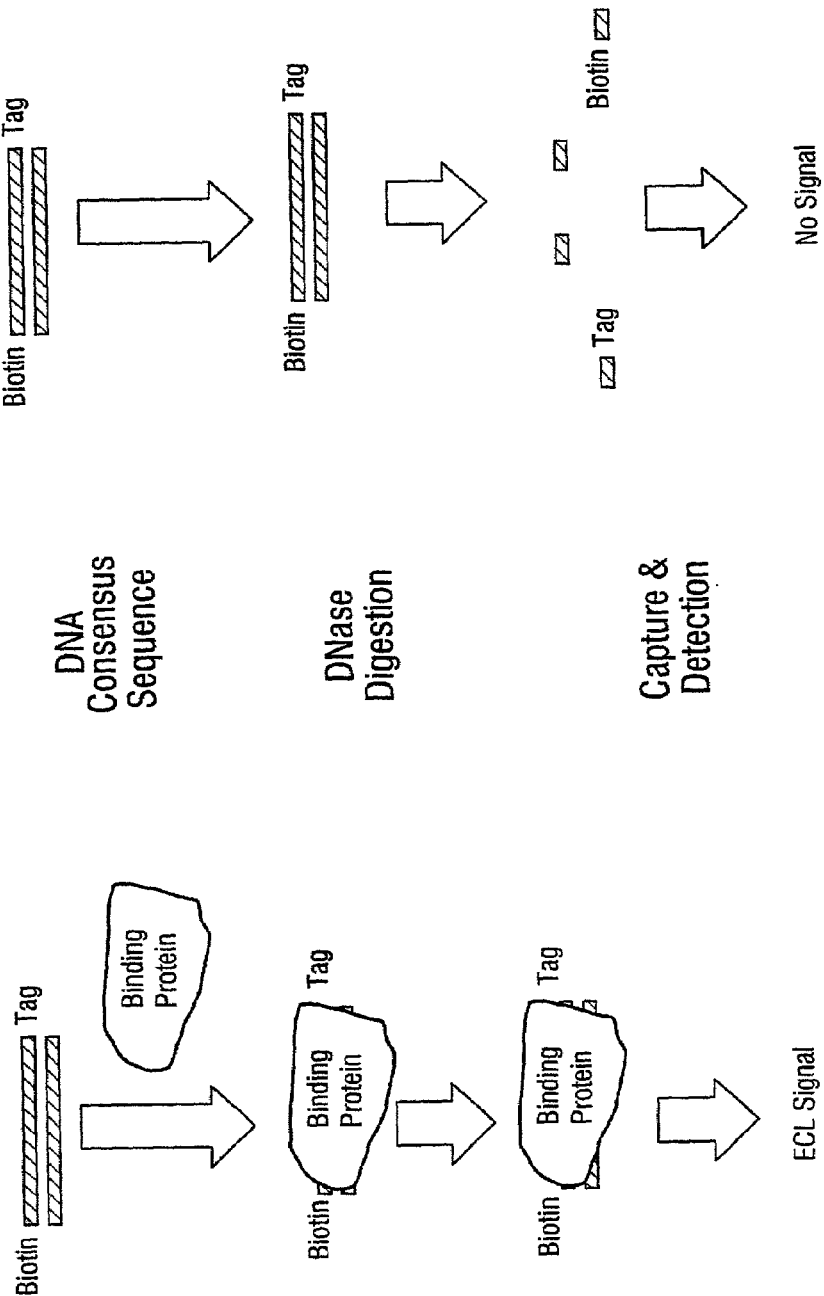
Fig. 7 Quantitation of DNA Binding Proteins using a Nuclease Protection Approach

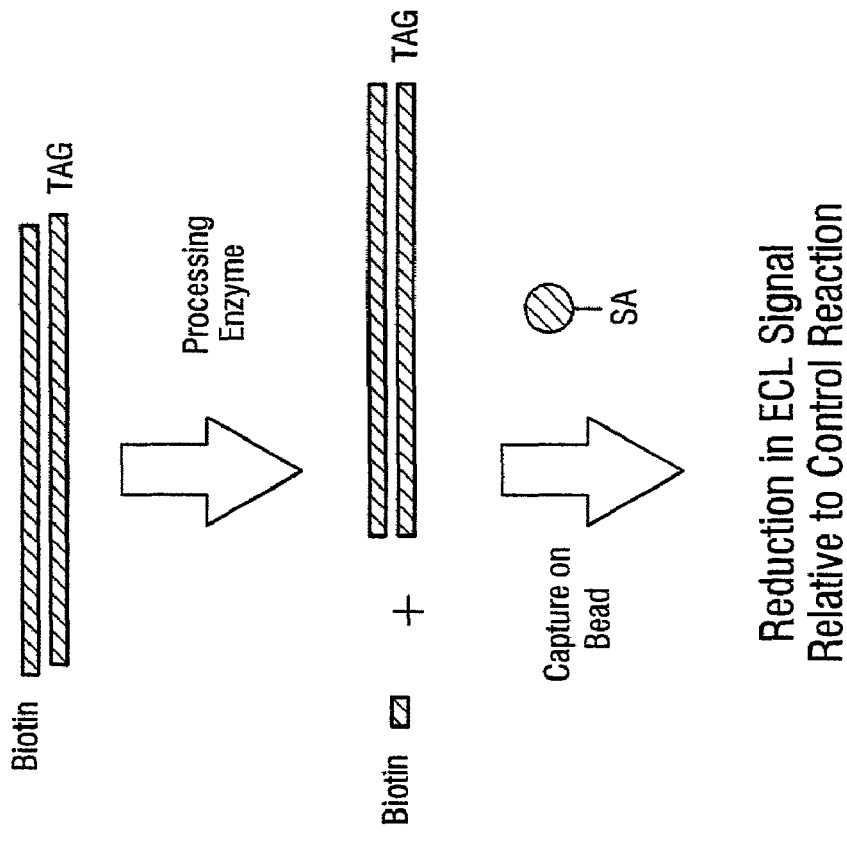

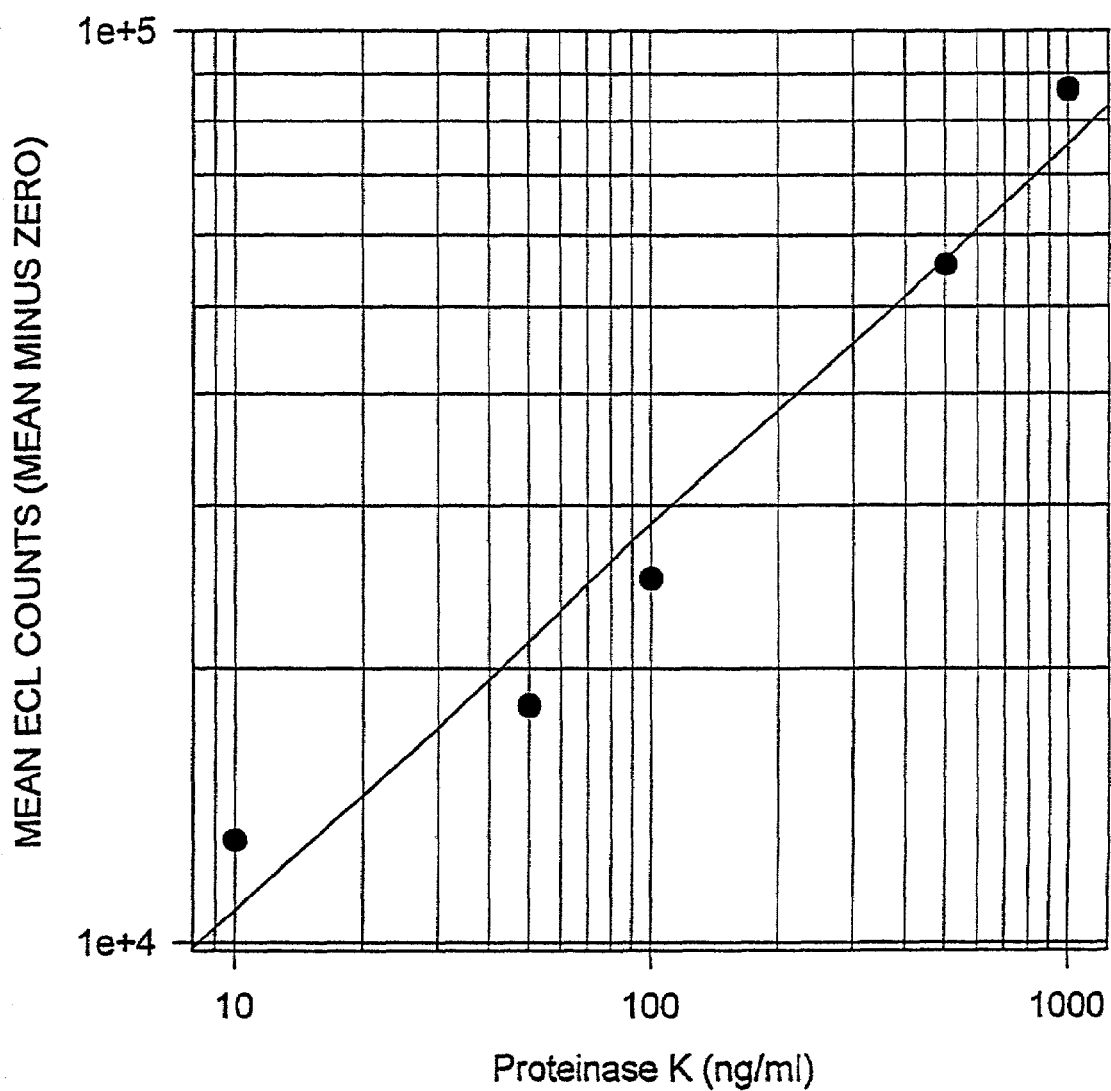
Fig. 9 An ECL-based Assay for the Measurement of Protease Activity

ASSAYS FOR MEASURING NUCLEIC ACID BINDING PROTEINS AND ENZYME ACTIVITIES

This application is a divisional of application Ser. No. 09/157,808, filed Sep. 17, 1998, allowed, now U.S. Pat. No. 6,312,896, issued Nov. 6, 2001, the entire content of which is hereby incorporated by reference in this application.

FIELD OF INVENTION

The present invention describes processes for measuring DNA or RNA binding proteins, specific nucleic acids, as well as enzyme activities using labeled nucleic acids or labeled protein/peptide molecules.

BACKGROUND OF INVENTION

The ability to measure the activity or amount of an analyte in a biological sample is critical in the fields of life sciences research and medical diagnostics. A broad class of important assays are assays that measure the activity of enzymes that catalyze the synthesis or cleavage of polypeptides or polynucleotides (or, similarly, assays for substrates, products or inhibitors of these enzymes). These enzymes include proteases, nucleases, polymerases, ligases and the like. Another broad class of important assays measure the interaction of nucleic acids with proteins or other nucleic acids.

Enzymatic activity may be measured through the use of synthetic enzyme substrates that show changes in color or fluorescence when acted upon by the enzyme. This approach, however, requires the design and synthesis of a custom reagent for every enzyme; a process that can be laborious, time consuming, and expensive. In addition, it is often desirable to measure the activity of an enzyme on its natural substrate.

A possibly more generic approach for measuring protease or nuclease activity is the Scintillation Proximity Assay (SPA); see, e.g., U.S. Pat. No. 4,568,649 and Published PCT Application WO90/03844. SPA uses small microspheres that are derivatized in such a way as to bind specific molecules. If a radioactive molecule is brought into close proximity to the bead a scintillant incorporated in the microsphere is excited and subsequently emits light. Radioactive molecules not bound to the microspheres excite the scintillant to a much lesser extent than radioactive molecules bound to the beads and, therefore, produce a weaker light signal. A number of assay formats have been described using SPA detection technology including protease (Wilkinson et al., *Pharm. Res.* (1993) 10, 562) and ribonuclease protection assays (Kenrick, et al., *Nucl. Acids Res.* (1997) 25, 2947).

While SPA has proved useful for these and other classes of assays, the technique has several disadvantages. The primary problem with SPA is the requirement for radioactive reagents. Because of the severe cost, safety, environmental, and regulatory issues associated with the use of radioisotopes, there is a clear need for alternative assay techniques that do not use radioactive materials. The background signal associated with the SPA approach is relatively high due to the inability of the assay format to totally discriminate the signal that is generated from free from that generated from bound radioactivity. In addition, the sensitivity of SPA has been found to be limited; there is a need for more sensitive assay techniques. As a result of the high background signal and low to moderate sensitivity, SPA approaches generally possess relatively low signal to noise ratios which, in many cases, can adversely effect assay performance.

The most common method for measuring the specific interaction of proteins with nucleic acids is the gel shift or electrophoretic mobility shift assay. This approach has been widely used for the study of sequence-specific binding proteins, especially transcription factors. The basis for the approach is that complexes of DNA and protein have a reduced or "shifted" mobility during non-denaturing gel electrophoresis. DNA duplexes, containing a specific protein binding sequence, are end labeled (generally with a radioactive label) and incubated with a sample containing the specific binding protein. The sample is subsequently analyzed by electrophoresis and the specific complexes are detected following autoradiographic analysis of exposed film. The amount of specific binding protein is determined semi-quantitatively by measuring the amount of the specific protein-DNA complex. This approach has been largely relegated to the world of basic exploratory research, primarily because of the inherent limitations of gel electrophoresis: i) the technique is complex and can usually only be carried out by highly trained lab technicians; ii) the technique is slow and laborious and is, therefore, not suited to the high throughput screening of large numbers of samples; and iii) the technique is, at best, semi-quantitative in nature. In addition, the use of radioactivity has also posed as an obstacle to some for the use of this technique. Although non-radioactive approaches have recently emerged, these approaches are accompanied by significant increases in labor.

Electrochemiluminescent Detection Technology

Numerous methods and systems have been developed for the detection and quantitation of molecules of interest in biochemical and biological samples. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon binding reactions, e.g., antigen-antibody reactions, nucleic acid hybridization techniques, protein-ligand systems as well as for formats for measuring a variety of enzymatic activities. The high degree of specificity in many biochemical and biological assay systems has led to many methods and systems of value in research and diagnostics. Typically, the existence of an analyte or enzyme of interest is indicated by the presence or absence of an observable "label" attached to one or more of the binding molecules or starting substrates.

Electrochemiluminescent (ECL) assays provide a sensitive and precise measurement of the presence and concentration of an analyte of interest. Such techniques use labels or other reactants that can be induced to luminesce when electrochemically oxidized or reduced in an appropriate chemical environment. Such electrochemiluminescence is triggered by a voltage impressed on a working electrode at a particular time and in a particular manner. The light produced by the label is measured and indicates the presence or quantity of the analyte. For a filler description of such ECL techniques, reference is made to U.S. Pat. Nos. 5,714,089, 5,591,581, 5,597, 910, 5,679,519, PCT published application WO90/05296, PCT published application WO92/14139, PCT published application WO90/05301; PCT published application WO96/24690, PCT published application US95/03190, PCT published application WO96/06946, PCT published application WO96/33411, PCT published application WO87/06706, PCT published application WO96/39534, PCT published application WO93/10267, PCT published application WO96/41175, PCT published application WO98/12539, PCT published application WO96/28538, PCT published application WO96/21039, PCT published application WO97/33176, PCT published application WO96/17248, and PCT published application WO96/40978, and U.S. patent application Ser. No. 09/023,483. The disclosures of the aforesaid applications are hereby incorporated by reference in their entirety. Reference is also made to two reviews on ECL technology: Blackburn et al. (Clinical Chemistry, 1991, 37, 1534-1539) and a 1994 review of the analytical applications of ECL by Knight, et al. (Analyst, 1994, 119: 879-890) and the references cited therein. The disclosure of the aforesaid articles are hereby also incorporated by reference in their entirety.

OBJECTS OF THE INVENTION

It is an object of the invention to provide a simple, accurate and reliable assay for measuring enzyme activity in a sample.

It is also an object of the invention to provide a simple, accurate and reliable assay for measuring proteins that bind nucleic acid.

It is an object of the invention to provide a simple, accurate and reliable assay for measuring inhibitors of enzyme activity in a sample.

It is an object of the invention to provide a simple, accurate and reliable assay for measuring substrates of enzymes in a sample.

It is an object of the invention to provide a simple, accurate and reliable assay for measuring specific nucleic acid sequences in a sample.

SUMMARY OF THE INVENTION

The present invention describes processes for measuring DNA or RNA binding proteins, specific nucleic acids, as well as enzyme activities using labeled nucleic acids or labeled protein/peptide molecules. As used herein, the term "measuring" or "measure" means detecting and/or quantitating.

This invention includes a method for measuring the amount or activity of an enzyme in a sample that catalyzes the cleavage of a molecule into two or more products, the method comprising the following steps: i) mixing a sample which may contain the enzyme with a substrate of the enzyme, an ECL label, and a solid phase, wherein the substrate is linked to the ECL label and is linked or capable of being linked to the solid phase and wherein the enzyme is capable of cleaving the substrate to form at least one product that is linked to an ECL label but that is not linked or capable of being linked to the solid phase; ii) inducing the mixture to emit electrochemiluminescence and iii) measuring the electrochemiluminescence so as to measure the amount or activity of the enzyme. The invention also includes analogous methods for measuring the amount or activity of substrates or inhibitors of enzymes that catalyze the cleavage of an enzyme into two or more products.

This invention includes a method for measuring the amount or activity of an enzyme that catalyzes the joining of two or more substrates to form a product, the method comprising the following steps: i) mixing a sample which may contain the enzyme with two substrates of the enzyme, an ECL label, and a solid phase, wherein one of the substrates is linked or capable of being linked to the solid phase and another of the substrates is not linked or capable of being linked to the solid phase but is linked to the ECL label and wherein the enzyme is capable of forming a product that is linked to the ECL label and linked or capable of being linked to the solid phase; ii) inducing the mixture to emit electrochemiluminescence and iii) measuring the electrochemiluminescence so as to measure the activity or amount of the enzyme. The invention also includes analogous methods for measuring the amount or activity of substrates or inhibitors of enzymes that catalyze the joining of two or more substrates to form a product.

This invention includes a method for measuring enzyme activities that cleave nucleic acid molecules in a sample, which comprises, mixing at least one or more single- or double-stranded nucleic acid molecules containing one or more ECL labels, adding a sample which may contain a nucleic acid-cleaving enzyme, and incubating under conditions which allow cleavage of the nucleic acid sequence, contacting this mixture with at least one solid phase, preferentially inducing ECL from ECL labels in solution or on the solid phase and measuring the ECL emission so as to measure the amount of cleaving activity in the sample. This invention includes a method for detecting and/or quantitating enzyme activities that cleave peptide or protein molecules in a sample, which comprises, mixing at least one or more peptide or protein molecules containing one or more ECL labels, contacting this mixture with at least one solid phase, adding a sample which may contain a peptide- or protein-cleaving enzyme, inducing ECL from ECL labels in solution and/or on the solid phase and measuring the ECL emission so as to measure the amount of cleaving activity in the sample.

This invention includes a method for measuring enzyme activities that covalently join nucleic acid molecules in a sample, which comprises, mixing at least one or more single- or double-stranded nucleic acid molecules containing one or more ECL labels, adding a sample which may contain a nucleic acid-joining enzyme, incubating under conditions which allow the joining of the nucleic acid sequences, contacting this mixture with at least one solid phase, inducing ECL from ECL labels in solution and/or on the solid phase and measuring the ECL emission so as to measure the amount of joining activity in the sample.

This invention includes a method for measuring enzyme activities that covalently join nucleic acid molecules in a sample, which comprises, mixing at least one or more single- or double-stranded nucleic acid molecules containing one or more ECL labels, contacting one or more of the labeled nucleic acid molecules with at least one solid phase, adding a sample which may contain a nucleic acid-joining enzyme, incubating under conditions which allow the joining of the nucleic acid sequences, inducing ECL from ECL labels in solution and/or on the solid phase and measuring the ECL emission so as to measure the amount of joining activity in the sample.

This invention includes a method for measuring nucleic acid binding proteins in a sample, which comprises the following steps: i) contacting the sample with one or more single- and/or double-stranded nucleic acid molecules containing a specific protein binding nucleotide sequence; ii) incubating under conditions which allow the specific binding of the nucleic acid binding proteins to the protein binding nucleotide sequence; iii) adding a nucleic acid cleaving reagent or enzyme; iv) incubating the sample under conditions that allow for the cleavage of the nucleic acid; and v) measuring the extent of nucleic acid cleavage.

This invention includes a method for detecting and/or quantitating nucleic acid binding proteins in a sample, which comprises, mixing at least one or more single- or double-stranded nucleic acid molecules containing a specific protein binding nucleotide sequence and containing one or more labels, contacting one or more of the labeled nucleic acid molecules with at least one solid phase, adding a sample which may contain one or more nucleic acid binding proteins, and incubating under conditions which allow the specific binding of the proteins to the protein binding nucleotide sequence, adding a nucleic acid cleaving reagent or enzyme, and incubating the sample under conditions that allow for the cleavage of the nucleic acid molecules, and measuring the amount of labeled nucleic acid on the solid phase and/or in the solution phase.

This invention includes a method for measuring nucleic acid binding proteins in a sample, which comprises the following steps: i) contacting the sample with one or more single- and/or double-stranded nucleic acid molecules containing a specific protein binding nucleotide sequence and containing a number of modified nucleotides that are resistant to nuclease digestion; ii) incubating under conditions which allow the specific binding of the proteins to the protein binding nucleotide sequence; iii) adding a nucleic acid cleaving reagent or enzyme; iv) incubating the sample under conditions that allow for the cleavage of the nucleic acid molecules; v) and measuring the extent of nucleic acid cleavage.

This invention includes a method for measuring nucleic acid binding proteins in a sample, which comprises the following steps: i) mixing at least one or more single- or double-stranded nucleic acid molecules containing a specific protein binding nucleotide sequence and containing a number of modified nucleotides that are resistant to nuclease digestion, and containing one or more labels; ii) contacting one or more of the labeled nucleic acid molecules with at least one solid phase; iii) adding a sample which may contain one or more nucleic acid binding proteins, and incubating under conditions which allow the specific binding of the proteins to the labeled nucleic acid sequences; iv) adding a nucleic acid cleaving reagent or enzyme, and incubating the sample under conditions that allow for the cleavage of the nucleic acid molecules, and measuring the amount of label on the solid phase and/or in solution.

This invention includes a method for measuring nucleic acid binding proteins in a sample, which comprises the following steps: mixing at least one or more single- or double-stranded nucleic acid molecules containing a specific protein binding nucleotide sequence, and containing a number of modified nucleotides that are resistant to nuclease digestion, and containing one or more labels; adding a sample which may contain one or more nucleic acid binding proteins, and incubating under conditions which allow the specific binding of the proteins to the labeled nucleic acid sequences; adding a nucleic acid cleaving reagent or enzyme, and incubating the sample under conditions that allow for the cleavage of the nucleic acid molecules; contacting one or more of the labeled nucleic acid molecules with at least one solid; and measuring the amount of labeled nucleic acid on the solid phase and/or in solution.

This invention includes a method for measuring nucleic acid binding proteins in a sample, which comprises the following steps: mixing at least one or more single- or double-stranded nucleic acid molecules containing a specific protein binding nucleotide, and containing a number of modified nucleotides that are resistant to nuclease digestion, and containing one or more labels; contacting one or more of the labeled nucleic acid molecules with at least one solid phase; adding a sample which may contain one or more nucleic acid binding proteins, and incubating under conditions which allow the specific binding of the proteins to the labeled nucleic acid sequences; adding a nucleic acid cleaving reagent or enzyme, and incubating the sample under conditions that allow for the cleavage of the nucleic acid molecules; and measuring the amount of labeled nucleic acid on the solid phase and/or in solution.

This invention includes a method for measuring specific nucleic acid sequences in a sample, which comprises, mixing at least one or more predetermined single-stranded nucleic acid molecules containing one or more ECL labels, contacting one or more of the labeled nucleic acid molecules with at least one solid phase, adding a sample which may contain one or more of the specific nucleic acid sequences, incubating under conditions which allow the specific binding of the sample nucleic acid sequences to the labeled nucleic acid sequences, adding a nucleic acid cleaving reagent or enzyme, incubating the sample under conditions that allow for the cleavage of the nucleic acid molecules, and detecting and/or quantitating the amount of labeled nucleic acid on the solid phase and/or in solution.

This invention also includes a method for measuring specific nucleic acid sequences in a sample, which comprises, mixing at least one or more predetermined single-stranded nucleic acid and containing one or more ECL labels, adding a sample which may contain one or more of the specific nucleic acid sequences, incubating under conditions which allow the specific binding of the sample nucleic acid sequences to the labeled nucleic acid sequences, adding a nucleic acid cleaving reagent or enzyme, incubating the sample under conditions that allow for the cleavage of the nucleic acid molecules, contacting one or more of the labeled nucleic acid molecules with at least one solid phase, measuring the amount of labeled nucleic acid on the solid phase and/or in solution.

BRIEF DESCRIPTION OF THE DRAWINGS

FIGS. 3(a), (b) and (c) show, schematically, three methods by which a substrate linked to a label and a binding reagent A can be contacted with a cleaving enzyme and a binding reagent B (on a solid phase) so as to form a first product linked to the label and a second product linked to the solid phase (by an A:B linkage).

FIGS. 5(a), (b), (c), (d), (e) and (f) illustrate six different embodiments of the invention for measuring the activity of cleaving enzymes.

FIG. 7 illustrates a method for measuring the interaction of a nucleic acid nucleic acid binding protein.

FIG. 8 illustrates a method for measuring the activity of nucleic acid cleaving enzyme.

FIG. 9 the ECL signal measured in an ECL-based protease assay as a function of the concentration of proteinase K.

DETAILED DESCRIPTION OF THE INVENTION

The subject invention relates to assays for enzymes that cleave a substrate into two or more products and/or join two or more substrates to form a product. The invention also includes assays for substrates and inhibitors of such enzymes. The enzyme activity is typically measured by the ability of the enzyme to modulate the ECL signal generated from an ECL label attached to a substrate molecule. The invention also includes reagents and kits for carrying out the methods of the invention. A kit for carrying out the methods of the invention can comprise, in one or more containers, at least two of the following components: enzyme, substrate, solid phase, buffers appropriate for carrying out the enzymatic reaction (e.g., mixtures of pH buffering substances, detergents, salts, metal ions, cofactors, proteins, sugars, excipients, and the like), solutions appropriate for carrying out an ECL measurement, solutions appropriate for cleaning and/or conditioning an ECL measuring device, ECL labels, calibration solutions containing known concentrations of an enzyme, calibration solutions containing a known concentration of an enzyme inhibitor, and calibration solutions for calibrating the response of an ECL measuring instrument. Suitable containers for such a kit include, but are not limited to vials, bottles, boxes, tubes blister packs, cartridges, syringes, microtiter plates, ampules, and the like.

Figure 1:
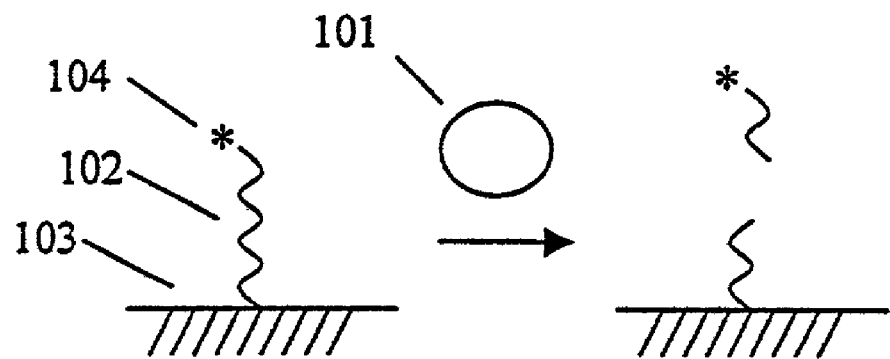
FIG. 1 shows, schematically, an enzyme cleaving a substrate, which is linked to a solid phase and a label, to form a first product linked to the label and a second product linked to the solid phase.
Figure 2:
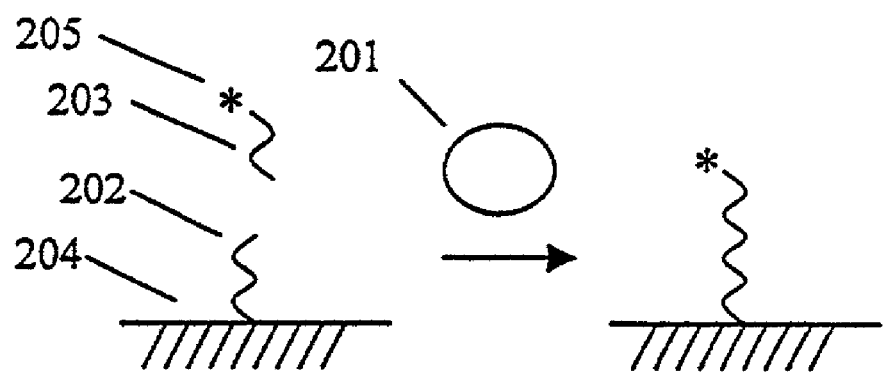
FIG. 2 shows, schematically, an enzyme joining a substrate linked to a solid phase with a substrate linked to a label, thereby, forming a product linked to both the label and solid phase.

As illustrated in FIG. 1, an enzyme 101 that catalyzes a cleavage reaction can be assayed through the use of a substrate 102 that is linked to both a solid phase 103 and an ECL label 104, so that the enzyme acts to separate the ECL label from the solid phase. The activity of the enzyme can be measured by an ECL measurement of the reduction of the number of ECL labels on the solid phase and/or an ECL measurement of the increase in the number of ECL labels in solution. In a different embodiment, illustrated in FIG. 2, an enzyme 201 that catalyzes the joining of two or more substrates is assayed through the use of a substrate 202 that is linked to a solid phase 204 and another substrate 203 that is linked to an ECL label 205, so that the enzyme acts to join the two substrates and, therefore, link the ECL label to the solid phase. The activity of the enzyme can be measured by an ECL measurement of the increase of the number of ECL labels on the solid phase and/or an ECL measurement of the decrease in the number of ECL labels in solution.

The Solid Phase and Linking of Substrates

The term "solid phase" is understood to encompass a wide variety of materials including solids, semi-solids, gels, films, membranes, meshes, felts, composites, particles, and the like. The solid phase can be non-porous or porous. Suitable solid phases include those developed and/or used as solid phases in solid phase binding assays (see, e.g., chapter 9 of Immunoassay, E. P. Diamandis and T. K. Christopoulos eds., Academic Press: New York, 1996, hereby incorporated by reference).

Figure 4A:
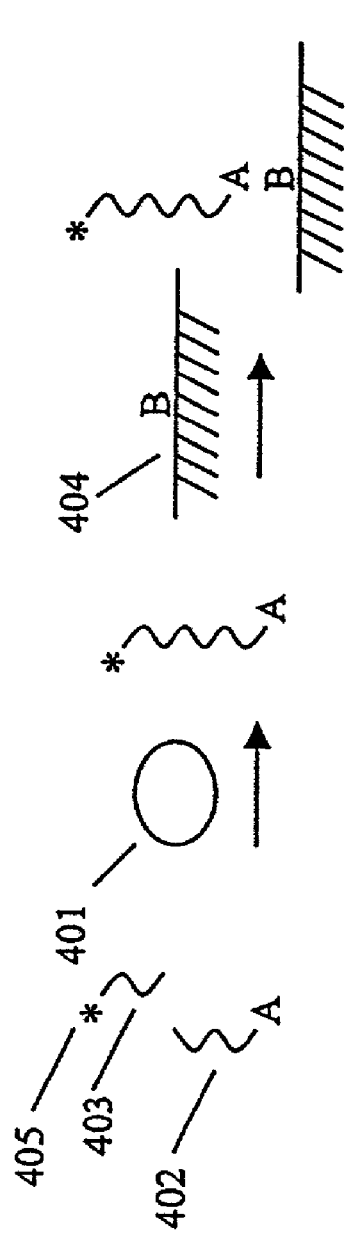
FIGS. 4(a), (b) and (c) show, schematically, three methods by which a first substrate, linked to a binding reagent A, and a second substrate, linked to a label, can be contacted with a joining enzyme and a binding reagent B (on a solid phase) so as to form a product linked to both the label and the solid phase (by an A:B linkage).
Figure 4B:
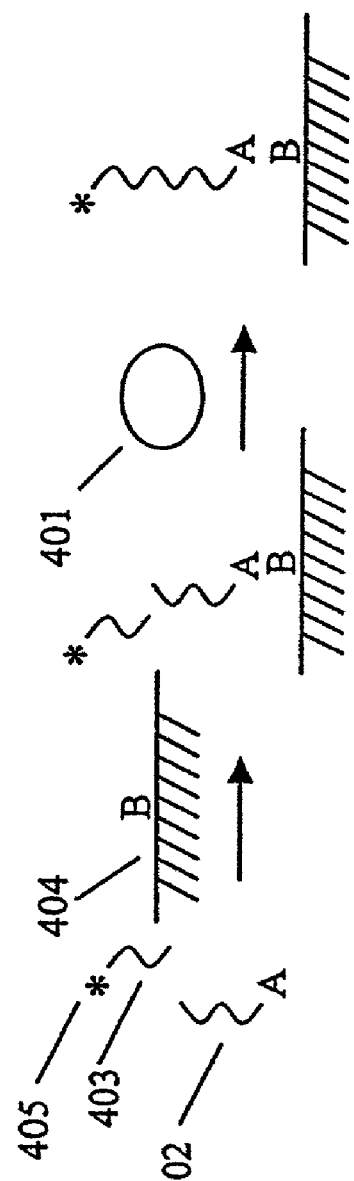
Figure 4C:
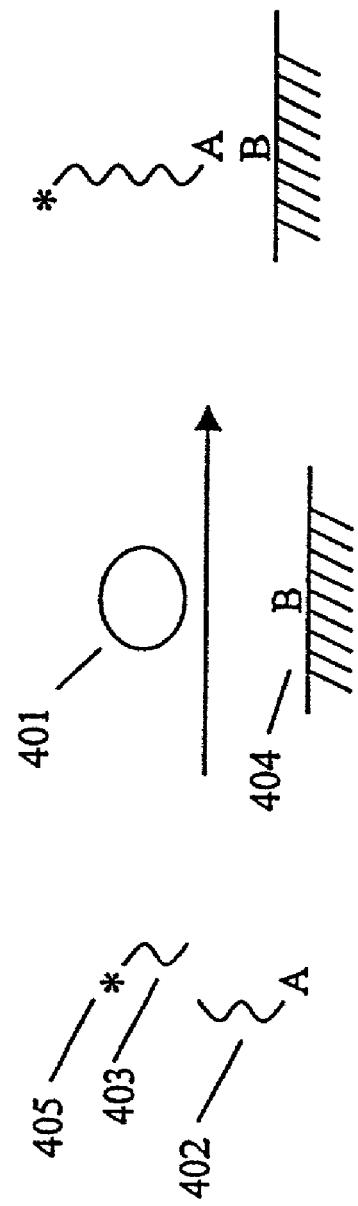

Methods for linking substrate molecules (e.g., polypeptides, polynucleotides, and polysaccharides) to solid phases are well known and include methods used for immobilizing reagents on solid phases for solid phase binding assays or for affinity chromatography (see, e.g., Diamandis and Christopoulos, cited above, and Hermanson, Greg T., Immobilized Affinity Ligand Techniques, Academic Press: San Diego, 1992, hereby incorporated by reference). These methods include the non-specific adsorption of molecules on the reagents on the solid phase as well as the formation of a covalent bond between the reagent and the solid phase. Alternatively, a substrate can be linked to a solid phase through a specific interaction with a binding group present on the solid phase (e.g., an antibody against a peptide substrate or a nucleic acid complementary to a sequence present on a nucleic acid substrate). In an advantageous embodiment, a substrate or product labeled with a binding reagent A (also referred to as a capture moiety) is contacted with a second binding reagent B present on the surface of a solid phase, so as to link the substrate to the solid phase through an A:B linkage. This approach is illustrated in FIGS. 3a-c (for assays of the activity of substrate cleaving enzymes) and FIGS. 4a-c (for assays of the activity of substrate joining enzymes). FIGS. 3a-c show that a substrate 302, linked to both a label 304 and a binding reagent A, can be contacted with a cleaving enzyme 301 prior to the formation of the A:B linkage (FIG. 3a), during the formation of the A:B linkage (FIG. 3b), or alternatively, after the formation of the A:B linkage (FIG. 3c) linking binding reagent A with a second binding reagent B present on the surface of the solid phase 303. Analogously, FIGS. 4a-c show that substrate 402, linked to a binding reagent A, and substrate 403, linked to a label 405, can be contacted with a joining enzyme 401 prior to the formation of the A:B linkage (FIG. 4a), during the formation of the A:B linkage (FIG. 4b), or alternatively, after the formation of the A:B linkage (FIG. 4c) linking binding reagent A with a second binding reagent B present on the surface of the solid phase 404. Many examples of A:B pairs that can be used to link molecules to a solid phase are known in the art, e.g., antibody-hapten pairs, receptor-ligand pairs, complementary nucleic acid pairs, metal-metal ligand pairs, etc. In an especially advantageous embodiment, the A:B linkage is a biotin streptavidin interaction.

Solid phases particularly useful for ECL binding assays have been described previously. One class of advantageous solid phases for ECL assays are particles. See published PC applications WO90/0530, WO89/04302, WO92/14138 and WO96/15440, said applications hereby incorporated by reference, for a description of particle-based reagents, methodology, and instrumentation for carrying out ECL binding assays using particles as a solid phase. These reagents, methodology and instrumentation can be adapted for use in ECL-based enzyme assays according to this invention. In an especially advantageous embodiment, magnetic particles (e.g., magnetic particles sold by Dynal, Seradyne, or Immunicon) are used as the solid phase. These particles can be collected at an ECL working electrode through the application of a magnetic field so as to preferentially cause the excitation of ECL from ECL labels linked to the particle, relative to ECL labels that are free in solution. Thus the amount of label on the solid phase can be measured in the presence of free label, labeled substrate, or labeled product in solution. Labels linked to magnetic particles can be induced to emit ECL preferentially (relative to labels in solution) by using a magnetic field to hold the particles on the electrode while free labels in solution are washed away. Alternatively, the labels in solution can be measured preferentially (relative to labels on magnetic particles) by capturing the magnetic particles on a magnet distant from the electrode used to induce ECL. There are several commercial instruments available that are capable of measuring the ECL emitted from magnetic particles collected, through the use of a magnetic field, at an electrode (e.g., ORIGEN, IGEN International; Elecsys, Boehringer-Mannheim; PicoLumi, Easai).

In an alternative embodiment, the solid phase is or comprises an electrode for ECL measurements. The use of such solid phase for ECL-based binding assays is described in PCT published application WO98/12539, hereby incorporated by reference in its entirety. The solid phases, instrumentation and methodology described in the above mentioned application can be adapted for use in the ECL-based enzyme assays of the present invention. Likewise, the methodology described in the above mentioned application for linking binding reagents to ECL electrodes can be applied to the substrates and products of the current application. Suitable solid phases include metal electrodes (e.g., gold and platinum), carbon electrodes (e.g., electrodes comprising glassy carbon, carbon black, graphite, carbon fibers, carbon nanotubes, and/or packed beds of carbon fibers or nanotubes), and organic polymer-based electrodes. An especially advantageous solid phase comprises a composite of carbon nanotubes in a polymer, e.g., a commercial plastic. Substrates and/or products can be linked to these and other solid phases by known methods including direct adsorption, covalent coupling, attachment to a film or coating on the solid phase (e.g., molecules can be immobilized on gold electrodes by attachment to a film of thiols coordinated to the gold surface, or silicon electrodes by attachment to a film of silanes covalently attached to silanols on the silicon surface), or by the formation of a specific A:B linkage (as was previously described in the present application). Advantageously, ECL labels in proximity to an electrode surface (e.g., labels linked to enzyme substrates or products present on the surface of the electrode) can be preferentially induced to emit ECL, relative to ECL labels that are free in solution. Thus the amount of label on the solid phase can be measured in the presence of free label, labeled substrate, or labeled product in solution. ECL labels in proximity to an electrode surface can even more preferentially be induced to emit ECL (relative to ECL labels in solution) by washing away the unbound label prior to inducing an ECL response. Alternatively, a solid phase distant from the electrode can be used to preferentially induce ECL from labels not on the solid phase.

Substrates can be immobilized on different regions of one or more solid phases to form a patterned array of substrates. Such a patterned array having two or more regions comprising substrates that differ in structure from each other could be used to simultaneously measure the activity of two or more enzymes (the substrates are chosen for their known specificity for a particular enzyme of interest). A similar patterned array of a library of substrates can be used to determine the substrate specificity of a particular enzyme. By the application of solutions containing an enzyme and an inhibitor to defined regions on a patterned array of substrates, large numbers of inhibitors can be rapidly screened for inhibitory ability. The measurement of the ECL from a patterned array can be conducted by imaging with an array of light detectors so that the ECL signal from different regions can be distinguished and independently measured. Alternatively, the substrates can be patterned on an array of independent electrodes so that labels in a particular region can be selectively induced to emit ECL by the selective application of voltage to selected electrodes. In this alternative embodiment, imaging is not necessary.

ECL Labels

An ECL label is a chemical substance that, when electrochemically oxidized or reduced under appropriate conditions, emits light. The term "ECL label" or "electrochemiluminescent label" refers to the substance itself, to a chemical derivative that has been modified to allow attachment to substrate or other reagent, or to a chemical derivative that is attached to a substrate or other reagent. The term "ECL label" also refers to the various products and/or intermediates formed from the label during the ECL-generating reaction. Numerous ECL labels have been reported in the literature (see the review by Knight et al., Analyst, 119, 879, 1994). Useful ECL labels include polyaromatic hydrocarbons (e.g., 9,10-diphenylanthracene, rubrene, phenanthrene, pyrene, and sulfonated derivatives thereof), organometallic complexes (e.g., complexes containing lanthanides, ruthenium, osmium, rhenium, platinum, chromium, and/or palladium), organic laser dyes, and chemiluminescent species (e.g., diacyl hydrazides such as luminol, acridinium esters, luiferase, and lucigenin). The ECL signal can be advantageously increased by using labels comprising a polymer or particle platform linked to a plurality of individual ECL labels (see, e.g., U.S. Pat. No. 5,679,519). Advantageous ECL labels are luminol and polypyridyl (especially bipyridyl or phenanthrolyl)-containing complexes of ruthenium, osmium or rhenium (see, e.g., the complexes described in U.S. Pat. Nos. 5,714,089, 5,591,581, 5,597,910, and published PCT application WO87/06706. The most advantageous ECL labels are ruthenium tris-bipyridyl (RuBpy) and its derivatives. The term "RuBpy" refers to the substance itself, to a chemical derivative that has been modified to allow attachment to substrate or other reagent substrate (e.g., derivatives comprising one or more of the following substituents: alkyl groups, amines, carboxylic acids, active esters or other activated carboxylic acid derivatives, phosphoramidites, hydrazides, alcohols, $\alpha,\beta$-unsaturated carbonyls, aldehydes, ketones, halides or other leaving groups, thiols, disulfides and the like), or to a chemical derivative that is attached to a substrate or other reagent. The term "RuBpy" also refers to the various products and/or intermediates formed from the label during the ECL-generating reaction. RuBpy includes ruthenium tris-bipyridyl coupled to a variety of different types of biomolecules to form highly ECL active conjugates. The ECL generated by oxidizing or reducing an ECL label at an electrode is known, for many ECL labels, to be dramatically increased by the addition of another species (the ECL coreactant) that is also oxidized or reduced at the electrode (generally, to give a reactive species that participates in a highly energetic reaction with the oxidation or reduction product of the ECL label). For example, hydrogen peroxide acts as an ECL coreactant for luminol. There are several classes of useful ECL coreactants for RuBpy, its derivatives, and the analogous osmium complexes, including: persulfate, oxalate, pyruvate (and other $\alpha$-keto carboxylic acids), and amines (especially, tertiary amines). An advantageous method for inducing ECL from RuBpy-containing substances in biological assays is oxidation of the ECL label in the presence of a solution containing tripropylamine.

The Enzymes

The term "enzyme" is understood to cover all polypeptides (or analogs thereof) with catalytic activity (including naturally occurring enzymes, genetically modified enzymes, chemically modified enzymes, catalytic antibodies, enzyme fragments and synthetic polypeptides), as well as nucleic acids (or analogs thereof) with catalytic activity (including ribosomes, ribosomal RNA, and ribozymes), synthetic enzyme models or mimics (for example, synthetic molecules designed to mimic the catalytic site of an enzyme), and enzyme cofactors that retain catalytic activity in the absence of a protein component. The enzymes that can be measured by this technique include enzymes that cleave a substrate molecule into two or more products and/or enzymes that join two or more substrates into a product. The enzymes can have both joining and cleaving activity, as in the following examples: i) a cleaving or joining enzyme that also catalyzes the reverse reaction (e.g., under appropriate conditions, proteases such as trypsin can catalyze the formation of amide bonds) and ii) the enzyme (e.g., a transferase) catalyzes the transfer of a moiety from a first substrate (i.e., cleaving the moiety from the first substrate) to a second substrate (i.e., joining the moiety to the second substrate). Advantageously, the enzymes break or form a covalent bond. Especially advantageous enzymes are enzymes that break or form a covalent bond type from the following list: amide bond, ester bond, phosphodiester bond (e.g., the bond linking nucleotides in a polynucleotide), and disulfide bond. Some examples of classes of enzymes that can be measured include the following: amidases, proteases, peptidases, glycosidases, saccharases, glycopeptidases, nucleases (including ribonucleases and deoxyribonucleases), endonucleases (including restriction endonucleases), exonucleases, ribosomes, ribosomal RNA, ribozymes, self-splicing molecules such as introns or inteins, esterases, phosphodiesterases, phosphorylases, AP endonucleases, polymerases (e.g., DNA or RNA polymerases), nucleic acid repair proteins, amino peptidases, carboxy peptidases, aminoacyl-tRNA synthetases, ADP-ribosyl transferases, proteases of the complement pathway, proteases of the thrombolytic pathways, transferases, endoglycosidases, exoglycosidases, lipases, endoproteinases, glutathione S-transferases, polysaccharide or oligosaccharide synthases (e.g. glycosyl transferases or glycogen synthases), ligases, ubiquitin-protein ligases, trans-glutaminases, integrases, and DNA glycosylases (e.g., uracil-DNA glycosylases). The invention is not limited to enzymes that catalyze the formation or cleavage of covalent bonds; the invention also covers enzymes that catalyze the formation or cleavage of non-covalent bonds or binding interactions, e.g., enzymes that catalyze the hybridization or dehybridization of nucleic acids (RecA and the like), proteins that catalyze or promote the association of proteins (e.g., Factor Va), peptides, and/or nucleic acids to form a complex, and proteins that catalyze the association of the peptide subunits of a protein to form a protein. The enzyme can catalyze a reaction that indirectly leads to the joining or cleavage of substrate molecules, e.g., the enzyme can catalyze a change in a substrate (e.g., phosphorylation of a protein) that induces the substrate to bind to a second molecule (e.g., a receptor specific for the phosphorylated substrate). Similarly, the enzyme could catalyze a change in a substrate (e.g., phosphorylation of a protein or modification of a nucleic acid, that could target the substrate for degradation by a second enzyme or reagent). In another such embodiment, the enzyme converts a substrate from an inactive form to a catalytically active form capable of cleaving or joining activity (e.g., Factor Xa can be measured from its ability to convert the inactive prothrombin into the catalytically active cleaving enzyme thrombin, which is in turn measured through its ability to cleave a peptide substrate). The invention is not only limited to measuring the activity of joining or cleaving enzymes but can also be used to measure the activity of other reagents with similar activity, e.g., metal complexes or oxidizing agents, photoactive cleaving or crosslinking agents, alkylating agents, acids, bases and the like that, that cleave bonds in nucleic aicds, proteins, or polysaccharides (see, e.g., the following publications, hereby incorporated by reference: Grant et al. Biochemistry, 1996, 35, 12313-12319; U.S. Pat. No. 4,980,473; and Biochemistry, G. Zubay, Ed., Addison-Wesley: Massachusetts, 1983).

The Substrates

The "substrates" that can be measured by the invention include substrates that are cleaved by an enzyme into two or more products and/or substrates that are joined by an enzyme into a product. Advantageously, the substrates comprise polypeptides, polysaccharides, nucleic acids, amino acids, nucleotides, and/or sugars. The terms polypeptides and polysaccharides are understood to encompass, respectively, oligopeptides and oligonucleotides. The term nucleic acids is understood to encompass oligonucleotides and polynucleotides. The substrates can comprise analogs of polypeptides, polysaccharides, nucleic acids, amino acids, nucleotides, and/or sugars, e.g., i) polypeptides comprising unnatural amino acids, N-methyl amide linkages, and/or non-amide linkages; ii) nucleic acid analogs comprising non-phosphodiester linkages e.g., amide bonds (i.e., peptide nucleic acids—PNAs), phosphorothioate linkages, and/or methyl phosphonate linkages; or iii) polysaccharides comprising non-glycosidic linkages (e.g., thioglycosides). In some embodiments, the substrates can be polypeptides, polynucleotides, or polysaccharides that comprise both natural and unatural monomer units; the catalytic activity of cleaving or joining enzymes can by this method be restricted to the natural components of the substrate. The number of unnatural monomer units in a substrate is advantageously between 1 and 999. In assays of the activity of enzymes that take modified nucleic acids or proteins as substrates (e.g., proteases specific for phosphorylated proteins or peptides, protesases specific for ubiquitinated proteins or peptides, DNA repair enzymes, etc.), the substrates can include the modified sites recognized by the enzymes (e.g., phosphorylated amino acids, ubiquinated amino acids, methylated nucleotide base, alkylated nucleotide bases, oxidized bases (e.g., 8-hydroxyguanine), cross-linked nucleic acid strands, thymidine dimers, 6+4 photoproducts, nucleic acids with apurinic or apyrimidinic sites, etc).

Substrates, advantageously, have functional groups (e.g., amino groups, carboxylic acids, active esters, acid halides, hydroxyls, ketones, aldehydes, olefins, $\alpha,\beta$-unsaturated carbonyls, $\alpha$-halocarbonyls, hydrazides, imidazoles, thiols, disulfides, halides or other leaving groups, photoactivatable groups, etc.) that allow for the convenient chemical linkage of the substrate to i) ECL labels, ii) solid phases, and/or iii) binding groups (e.g., biotin) that allow attachment to complementary binding groups (e.g., streptavidin) on a solid phase. For a list of some useful linking chemistries and reagents, see the Pierce Chemical Company Catalog and Handbook for 1994-1995 (Pierce Chemical Co., Rockford, Ill.) and Hermanson, Greg T. *Bioconjugate Techniques* Academic Press: New York, 1996, said publications hereby incorporated by reference. The labeling and/or immobilization of the substrate can be achieved by chemical treatment of the substrate molecule with functional groups present on the label and/or solid phase (e.g., amino groups, carboxylic acids, active esters, acid halides, hydroxyls, ketones, aldehydes, olefins, $\alpha,\beta$-unsaturated carbonyls, $\alpha$-halocarbonyls, hydrazides, imidazoles, thiols, disulfides, halides, photoactivatable groups, etc.). By using standard coupling chemistries known in the art, it is possible to conveniently label/immobilize the natural substrate of an enzyme (the cost, labor, and uncertainty of using unnatural or synthetic substrates can be avoided). Control over the sites of labeling/immobilization can be achieved by using coupling chemistries specific for a particular functionality on a substrate (e.g., an oligonucleotide that is 5'-modified with an amino group and 3'-modified with a thiol group can be specifically labeled at the 5' position with the NHS ester of biotin, and specifically labeled at the 3' position with a maleimide derivative of RuBpy). In an alternative embodiment, the substrate is chemically or enzymatically synthesized using labeled (and/or chemically modified) components so as to introduce labels (and/or points of attachment). For example, labeled or chemically modified amino acids can be introduced into defined positions of a polypeptide by solid phase synthesis. Similarly, labeled or chemically modified nucleotides (or phosphoramidites) can be introduced into defined positions of a polynucleotide by solid phase synthesis. In one embodiment, the solid phase support used in the synthesis of substrates by solid phase synthesis is also used as the solid phase of the ECL enzyme assay. In a different example, a polynucleotide substrate is synthesized through a polymerase reaction run in the presence of labeled and/or chemically modified nucleotides.

Cleaving Enzymes

The activity of cleaving enzyme is determined by measuring the effect of the enzyme on the concentrations or amounts of an ECL label in solution or on a solid phase. FIGS. 5a-f illustrate different embodiments of the invention. The illustrated embodiments are similar in that the enzyme 501 cleaves at least one linkage in a substrate 502, the linkage linking one or more ECL labels 503 with a solid phase (or alternatively a moiety capable of being immobilized on a solid phase) 504. The enzyme can cleave one linkage in the substrate (FIGS. 5a,c,e) or more than one linkage (FIGS. 5b, d). The substrate can comprise one ECL label (FIGS. 5a,b) or more than one ECL label (FIGS. 5d-f). The products can include more than one solution-phase product comprising an ECL label (FIGS. 5d-e) as well as solution-phase products not comprising an ECL label (FIG. 5b). An individual product can comprise more than one ECL label (FIG. 5c). The reactions can require additional substrates that are not shown and/or could form additional products that are not shown. FIG. 5f shows an assay for an enzyme with transferase activity; the cleaved portion of the substrate is transferred to a second substrate 505.

Joining Enzymes

Figure 6A:
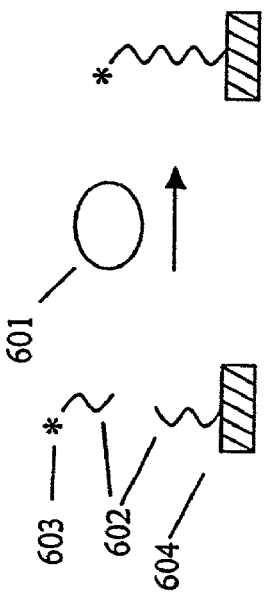
FIGS. 6(a), (b), (c), (d) and (e) illustrate five different embodiments of the invention for measuring the activity of joining enzymes.
Figure 6B:
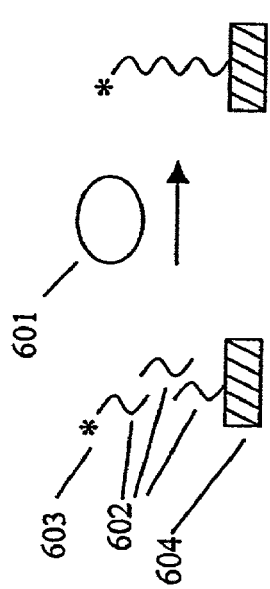
Figure 6C:
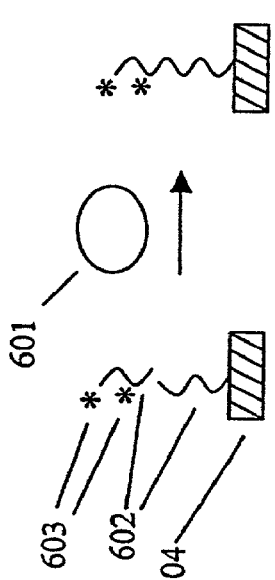
Figure 6D:
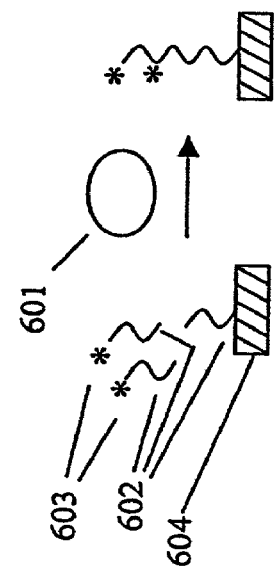
Figure 6E:
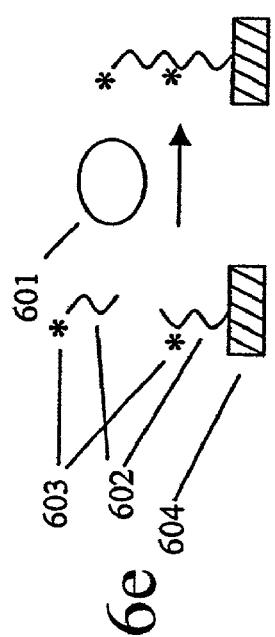

The activity of a joining enzyme is also determined by measuring the effect of the enzyme on the concentrations or amounts of an ECL label in solution or on a solid phase. FIGS. 6a-e illustrate different embodiments of the invention. The illustrated embodiments are similar in that the enzyme 601 forms at least one linkage joining substrates 602, the linkage linking one or more ECL labels 603 with a solid phase (or alternatively a moiety capable of being immobilized on a solid phase) 604. The enzyme can form one linkage in the product (FIGS. 6a,c,e) or more than one linkage (FIGS. 6b, d). The product can comprise one ECL label (FIGS. 6a,b) or more than one ECL label (FIGS. 6d-f). The substrates can include more than one solution-phase substrate comprising an ECL label (FIGS. 6d-e) as well as solution-phase substrates not comprising an ECL label (FIG. 6b). An individual substrate can comprise more than one ECL label (FIG. 6c). The reactions can require additional substrates that are not shown and or form additional products that are not shown.

Joining activity can be measured that joins a plurality of substrates to form a large aggregate. For example, thrombin can be measured by using a substrate mixture containing fibrinogen labeled with an ECL label and fibrinogen linked to a solid phase (or alternatively to a capture moiety). The enzyme activity converts the fibrinogen into a fibrin clot comprising a plurality of fibrin monomers; the clot comprises both ECL labels and links to one or more solid phases (or one or more capture moieties). The thrombin activity is, therefore, directly related to the quantity of ECL labels on a solid phase or linked to a capture moiety. The fibrin clot dissociates in dilute acid, but the transglutaminase $A_2$ crosslinks the fibrin clot to form an acid-stable clot. Transglutaminase $A_2$ in a sample can, therefore, be measured by treating the sample with a thrombin induced clot (prepared as in the abovementioned thrombin assay) as a substrate and measuring the quantity of ECL labels on the solid phase after treatment of the clot with dilute acid. Transglutaminase $A_2$ also joins other proteins to fibrin during clot formation (e.g., $\alpha_2$-antiplasmin and Factor V). By analogy to the general scheme for measuring joining enzymes, transgluminase can be measured, e.g., by its activity for joining fibrin labeled with an ECL-label and $\alpha_2$-antiplasmin into a clot. See Blood: Principles and Practice of Hematology, R. Handin et al., Eds., J. B. Lippencott Co.: Philadelphia, 1995, hereby incorporated by reference, for more information on joining and cleaving enzymes present in blood).

Enzyme Assays

The invention can be used to assay an enzyme of interest. Generally, such an assay involves mixing a sample containing an unknown quantity of the enzyme with a predetermined quantity of one or more substrates and determining the amount or activity of the enzyme through a measurement of ECL. The invention can also be used to measure conditions or factors that can influence the activity of an enzyme, e.g., temperature, pH, enzyme inhibitors, denaturing compounds, enzyme activators, enzyme deactivators and the like.

Enzyme Inhibition Assays

The invention can also be used to assay an enzyme inhibitor and/or to measure the inhibitory ability of test compound. Generally, such an assay involves mixing a sample of unknown inhibitory ability (e.g., a sample containing an unknown quantity of a known inhibitor or a sample containing a test compound) with a predetermined quantity of an enzyme and one or more substrates, and determining the ability of the sample to inhibit the enzyme through a measurement of ECL.

Assays for Enzyme Substrates

The invention can also be used to assay an enzyme substrate. Generally, such an assay involves mixing a sample containing an unknown quantity of an enzyme substrate with a predetermined quantity of an enzyme (and, if required, one or more additional substrates) and measuring the formation of product through an ECL measurement. The invention can also be used to determine if a substance is accepted as a substrate by an enzyme. Generally, such an assay involves mixing a sample containing a possible enzyme substrate with a predetermined quantity of an enzyme (and, if required, one or more additional substrates) and measuring the formation of product through an ECL measurement.

Furthermore, the invention can be used to monitor a second reaction (in addition to the enzyme reaction) that modulates the amount of an enzyme substrate and/or the ability of a substrate to act as a substrate in the enzyme reaction. The ECL enzyme assay is used, e.g., to measure the presence of substrates, products, or catalysts of the second reaction. In one such embodiment, the ability of a substance to act as a substrate for an enzyme is modulated as the result of a binding reaction (i.e., said second reaction is a binding reaction). In the case of nucleic acids as substrates for nucleases, these binding reactions include: the binding of a single stranded nucleic acid with a complementary nucleic acid sequence; the binding of a double stranded nucleic acid with a triple helix forming molecule such as a nucleic acid, a peptide nucleic acid (PNA), a minor or major groove binding peptide (e.g., distamycin and polyamides containing hydroxypyrrole, imidazole and/or pyrrole such as those described in White et al. Nature, 1998, 391, 468, hereby incorporated by reference), and/or a nucleic acid binding protein. In one example, the ability of a ribonuclease specific for single stranded RNA to cleave a first RNA sequence is modulated by the presence of a complementary sequence that can participate in a hybridization reaction with the first sequence; this effect provides the basis for the measurement of the complementary sequence in a sample. In a second example, the binding of a nucleic acid binding protein to a nucleic acid can block the ability of a nuclease to cleave the nucleic acid; this effect can be used to determine the quantity, binding ability, or specificity of a nucleic acid binding protein in a sample. The effect can also be used to measure the ability of a sample (or components of a sample) to inhibit the interaction between a nucleic acid and a nucleic acid binding protein.

Enzymes (e.g., proteases specific for phosphorylated proteins or peptides, protesases specific for ubiquitinated proteins or peptides, DNA repair enzymes, etc.), that take modified nucleic acids or proteins as substrates (e.g., phosphorylated amino acids, ubiquinated amino acids, methylated nucleotide base, alkylated nucleotide bases, oxidized bases such as 8-hydroxyguanine, cross-linked nucleic acid strands, thymidine dimers, 6+4 photoproducts, nucleic acids with apurinic or apyrimidinic sites, etc.) can be used to measure these substrates and, therefore, to measure enzymes, drugs, reagents, toxins, and/or conditions that cause or repair these modifications (e.g., the causation or repair of said modifications can be the above mentioned second reaction).

Kits for Carrying Out the Methods of the Invention

The invention also includes reagents and kits for carrying out the methods of the invention. A kit for carrying out the methods of the invention can comprise, in one or more containers, at least two of the following components: enzyme, substrate, solid phase, buffers appropriate for carrying out the enzymatic reaction (e.g., mixtures of pH buffering substances, detergents, salts, metal ions, cofactors, proteins, sugars, excipients, and the like), solutions appropriate for carrying out an ECL measurement, solutions appropriate for cleaning and/or conditioning an ECL measuring device, calibration solutions containing known concentrations of an enzyme, calibration solutions containing a known concentration of an enzyme inhibitor, and calibration solutions for calibrating the response of an ECL measuring instrument. These components can be supplied in dry and/or liquid form. Kits for measuring the interaction between nucleic acids and a nucleic acid binding protein can additionally include one or more of the following components: nucleic acid substrate, nucleic acid binding protein, calibration solutions containing known amounts of a DNA binding protein, calibration solutions containing a known amount of a nucleic acid substrate, or calibration solutions containing a known amount of an inhibitor of a protein-nucleic acid interaction.

Assay Formats

A. Method for Assaying a Sample for the Presence of a Nucleic Acid Binding Protein In one embodiment of the present invention, the interaction of a nucleic acid binding protein with a nucleic acid is measured using a nuclease or chemical protection approach. This approach makes use of the ability of a nucleic acid binding protein, when bound to a nucleic acid, to protect (fully or partially) the phosphodiester backbone of the nucleic acid from cleavage by a nucleic acid cleaving enzyme or reagent. The binding of the protein to the nucleic acid can be monitored by measuring the extent of the cleavage reaction (e.g., by measuring the decrease in the amount of substrate and/or the increase in the amount of product). The protection of a nucleic acid by a nucleic acid binding protein can be used to measure the amount of a nucleic acid binding protein in a sample, to measure the affinity of a binding protein for a nucleic acid sequence, to screen for peptides or proteins capable of binding a specific sequence, to screen for a nucleic acid sequence that is bound by a specific protein, and/or to screen for inhibitor substances that inhibit the interaction. The method is easily adaptable to use in high throughput screening. Libraries of compounds (e.g., substrates, proteins, peptides, inhibitors) include libraries of more than 100 compounds, or advantageously, libraries of more than 10,000 compounds, or most advantageously, libraries with more than 1,000,000 compounds.

The proteins or peptides that can be measured by this method include, but are not limited to, proteins that bind nucleic acids to regulate nucleic acid translation, transcription, reproduction, editing, localization, degradation, repair, etc. They also include triple helix-forming nucleic acid sequences, nucleic acid binding toxins, antibiotics, and regulatory proteins from bacteria, viruses, and other sources. The proteins or peptides can be from natural sources or manmade. The proteins can bind to specific nucleic acid sequences or alternatively can have limited or no sequence specificity.

Advantageously, the cleaving enzyme or reagent shows a greater than 20 fold preference for the unprotected nucleic acid vs. the protected nucleic acid. Enzymatic cleavage reagents (e.g. nucleases) can be selected by screening for enzymes according to their selectivity for the unprotected nucleic acid substrate of an assay. Non-enzymatic cleavage reagents include transition metal complexes capable of oxidizing nucleic acid (advantageously linked to a nucleic acid binding moiety or intercalater), photoactivated cleaving reagents, acids, bases, and the reagents used for cleaving DNA in Maxam-Gilbert sequencing (e.g., dimethylsulfate/heat/alkali, dimethylsulfate/acid/alkali, hydrazine/piperidine). In an alternate embodiment, the nucleic acid binding protein protects the nucleic acid from a chemical, enzymatic and/or photochemical modification—for example, methylation, alkylation (e.g., by a cancer therapeutic agent), oxidation (e.g., to form 8-hydroxyguanine), base excision, strand cross linking, formation of thymidine dimers, formation of 6+4 photoproducts, etc.) that make the nucleic acid more susceptible to a second enzyme or reagent that, e.g., cleaves nucleic acids (e.g., a methylated nucleic acid specific nuclease or an AP endonuclease).

The predetermined (except in the case of an enzyme activity with random specificity) nucleic acid substrates can be single or double stranded or comprise regions of both. Advantageously, the nucleic acid substrate is 4-1000 kilobases in length, more advantageously 4-100 kilobases in length, and most advantageously 4-30 kilobases in length. The nucleic acid substrate comprises a protein binding site, for example a sequence specific for a protein of interest; the substrate also comprises a site capable of being cleaved by a nucleic acid cleaving enzyme or reagent. Advantageously, the binding protein, nucleic acid substrate, and/or the cleaving enzyme/reagent are chosen so that the cleavage site lies within the protein binding site and the protective effect is maximized. In some cases there can be additional cleavage sites (e.g., sites falling outside of the protein binding site)) that are not sufficiently protected by the binding protein. These additional cleavage sites are advantageously protected from cleavage by the use of nucleic acid analogs that are resistant to cleavage, e.g., nucleotides that are linked by amide bonds (e.g., peptide nucleic acids), phosphorothioate bonds, or methyl phosphonate bonds. In an advantageous embodiment, the region of the nucleic acid within the protein binding site comprises nucleotides linked by phosphodiester bonds (advantageously such a region comprises from 2-100, more advantageously from 2-50, and most advantageously 4-14 nucleotides linked by phosphodiester bonds); the region outside the protein binding site comprises nucleotides linked by phosphorothioate bonds. Advantageously, a nucleic acid containing unnatural nucleotides comprises from 1 to 999 unnatural nucleotides.

The measurements of the decrease in the amount of substrate or the increase in the amount of product can be measured by any technique that can be used to measure a nucleic acid of e.g., a particular size, sequence, composition, and/or charge. For example substrates or products can be measured by chemical analysis (e.g., mass spectrometry, chromatography, electrophoresis, NMR, nucleic acid sequencing, etc.) or by hybridization (e.g., Northern blots, southern blots, solid phase binding assays, fluorescence energy transfer methods such as the use of molecular beacons, etc.—see, e.g., Nonradioactive Labeling and Detection of Molecules, Kessler, C., ed., Springer-Verlag: Berlin, 1992 and Keller, G. H.; Manak, M. M. DNA Probes, 2nd Ed., MacMillan Publishers Ltd.: London, 1993, each of these books, hereby, incorporated by reference).

Nucleic Acid Substrates that Comprise a Detectable Label and are Linked (or Capable of Being Linked) to a Solid Phase. In one embodiment of the invention's assays for nucleic acid-protein interactions, the nucleic acid substrate comprises one or more detectable labels and is also linked to a solid phase (or, alternatively, comprises one or more moieties capable of being captured at a solid phase, e.g., biotin, a specific nucleic acid sequence, a hapten, a ligand, etc.). The nucleic acid substrate is constructed in such a way that one or more of the labels are separated from the solid phase (or, alternatively, the capture moieties) by a sequence of nucleotides that comprise both a protein binding sequence and a site capable of being cleaved by a nuclease. The regions of the nucleic acid outside the protein binding site can advantageously comprise nucleotides linked by cleavage-resistant linkages (e.g., phosphorothioate linkages) to prevent cleavage of the nucleic acid in regions that can't be protected by the nucleic acid binding protein. In a protein binding assay, the nucleic acid substrate is mixed with the protein sample, advantageously in a buffer that promotes the association of the protein with the nucleic acid. The sample is subsequently mixed with a nucleic acid-cleaving enzyme, advantageously for a defined length of time and at a defined temperature. The amount of the detectable label on the solid phase or free in solution is then measured (if necessary, after capturing the capture moieties by contacting the mixture with a solid phase) to determine the extent of substrate cleavage and therefore the amount of protein-nucleic acid complex that formed. The binding of the protein to the nucleic acid results in an increase in the label on the solid phase and a decrease in the label in solution. Detectable labels that can be used include, but are not limited to, enzymes, radioisotopes, fluorescent labels, chemiluminescent labels, ECL labels, bioluminescent labels, electrochemically detectable labels, magnetic labels, optically detectable particles such as colloidal gold, etc. In one embodiment of the invention, an array of labeled nucleic acids is immobilized on a solid phase (advantageously an electrode), e.g., to determine the consensus sequence of one or more nucleic acid binding proteins in a sample. In this example, detectable labels on array elements comprising a consensus sequence are protected from treatment with a nuclease and remain largely on the solid phase, while detectable labels on array elements without a consensus sequence are cleaved off by treatment with a nuclease.

Nucleic Acid Substrates that Comprise an ECL Label and are Linked (or Capable of Being Linked) to a Solid Phase. In a advantageous embodiment of the invention's assays for nucleic acid-protein interactions (illustrated in FIG. 7), the nucleic acid substrate comprises one or more ECL labels and is also linked to a solid phase (or, alternatively, comprises one or more moieties capable of being captured at a solid phase, e.g., biotin, a specific nucleic acid sequence, a hapten, a ligand, etc.). Advantageous ECL labels include luminol and bipyridyl- or phenanthrolyl-containing complexes of Ru, Os and Re. An especially advantageous label is RuBpy. The nucleic acid substrate is constructed in such a way that one or more of the labels are separated from the solid phase (or, alternatively, the capture moieties) by a sequence of nucleotides that comprise both a protein binding sequence and a site capable of being cleaved by a nuclease. The regions of the nucleic acid outside the protein binding site can advantageously comprise nucleotides linked by cleavage-resistant linkages such as phosphorothioate linkages to prevent cleavage of the nucleic acid in regions that can't be protected by the nucleic acid binding protein. In a protein binding assay, the nucleic acid substrate is mixed with the protein sample, advantageously in a buffer that promotes the association of the protein with the nucleic acid. The sample is subsequently mixed with a nucleic acid-cleaving enzyme, advantageously for a defined length of time and at a defined temperature. The amount of the detectable ECL label on the solid phase or free in solution is then measured (if necessary, after capturing the capture moieties by contacting the mixture with a solid phase) to determine the extent of substrate cleavage and therefore the amount of protein-nucleic acid complex that formed. The binding of the protein to the nucleic acid results in an increase in the label on the solid phase and a decrease in the label in solution. In one advantageous embodiment, the solid phase is a magnetic bead and the ECL label on the solid phase is measured after using a magnetic field to capture the beads on an electrode for inducing ECL, e.g., through the use of an ORIGEN analyzer. In a different advantageous embodiment, the solid phase is an electrode (e.g., a composite comprising carbon nanotubes in polymeric matrix) and the ECL label on the solid phase is measured by applying a potential at the electrode so as to induce the ECL labels to electrochemiluminesce. These measurements of ECL labels are highly quantitative, sensitive, and precise. Advantageously the assay has a detection limit (for measuring a nucleic acid binding protein, its nucleic acid partner, or an inhibitor of the interaction) of less than 1 nmol, more advantageously, the detection limit is less than 1 pmol, even more advantageously, the detection limit is less than 1 fmol, even more advantageously, the detection limit is less than 1 amol.

Nucleic Acid Substrates for Measuring DNA-Protein Interactions by the Fluorescence Resonance Energy Transfer (FRET) Technique. In another advantageous embodiment of the invention's assays for nucleic acid-protein interactions, the nucleic acid substrate is linked to one or more fluorescence energy donors and one or more fluorescence energy acceptors (one with skill in the art of FRET assays can select appropriate donors and acceptors and appropriate substrate structures for a particular assay so as to produce efficient energy transfer from donor to acceptor). In one embodiment of a FRET assay for measuring protein-nucleic acid interactions, the nucleic acid substrate is constructed in such a way that at least one of the donors is separated from at least one of the acceptors by a sequence of nucleotides that comprise both a protein binding sequence and a site capable of being cleaved by a nuclease. The regions of the nucleic acid outside the protein binding site can advantageously comprise nucleotides linked by cleavage-resistant linkages such as phosphorothioate linkages to prevent cleavage of the nucleic acid in regions that can't be protected by the nucleic acid binding protein. In a protein binding assay, the nucleic acid substrate is mixed with the protein sample, advantageously in a buffer that promotes the association of the protein with the nucleic acid. The sample is subsequently mixed with a nucleic acid-cleaving enzyme, advantageously for a defined length of time and at a defined temperature. The cleavage of the substrate leads to a decrease in the amount of fluorescence energy transfer due to an increase in the distance between the donor and acceptor moieties. This decrease in energy transfer can be measured by measuring the increase in the fluorescence intensity from the donor and/or by measuring the decrease in intensity of the acceptor (resulting from excitation of the donor). The more nucleic acid binding protein that is present, the less cleavage is observed and, therefore, the lower the fluorescence signal due to the donor and the higher the fluorescence signal due to the acceptor.

B. Method for Assaying a Sample for the Presence of an Enzyme Activity that Joins Nucleic Acids In another embodiment of the present invention, an enzyme of interest that forms nucleic acid linkages between nucleic acids and/or nucleotides is measured in a sample by combining the sample with at least one, advantageously two, predetermined (except in the case of an enzyme activity with random specificity) nucleic acid (and/or nucleotide) substrates, wherein at least one of said substrates comprises one or more ECL labels (advantageously luminol or bipyridyl- or phenanthroline-containing complexes of Ru or Os, most advantageously RuBpy) and at least one other of said substrate is linked to a solid phase (advantageously, a magnetic bead or an electrode). The nucleic acid substrates can be single or double stranded or comprise regions of both. Advantageously, the nucleic acid substrate is 4-1000 kilobases in length, more advantageously 4-100 kilobases in length, and most advantageously 4-30 kilobases in length. The substrates are designed or prepared so that the enzymatic reaction links at least one ECL label on a substrate to a solid phase. The extent of enzymatic joining is determined by a measurement of the ECL labels that couple to the solid phase. Increased enzymatic activity leads to an increase in the coupling of the ECL labels to the solid phase and, therefore, an increase in ECL signal. Alternatively, the extent of enzymatic cleavage can be determined by a measurement of the ECL labels that remain free in solution (e.g., the ECL from ECL labels in solution can be preferentially measured at an electrode in the presence of ECL labels present on particulate solid phases in suspension). In this alternative embodiment, increased enzymatic activity results in a decrease in ECL signal.

These measurements of ECL labels are highly quantitative, sensitive, and precise. Advantageously the assay has a detection limit (for measuring a nucleic acid cleaving enzyme, its substrates, or an inhibitor of the enzyme) of less than 1 nmol, more advantageously, the detection limit is less than 1 pmol, even more advantageously, the detection limit is less than 1 fmol, even more advantageously, the detection limit is less than 1 amol.

Advantageously, the enzyme sample is contacted with the nucleic acid and/or nucleotide substrates for a defined period of time under defined conditions (e.g., temperature, pH, etc.) prior to the ECL measurement. In alternate embodiments, the nucleic acid and/or nucleotide substrates do not include substrates that are linked to a solid phase but include substrates that comprise moieties that can be captured on a solid phase (e.g., biotin, specific nucleic acid sequences, ligands or haptens). The substrate can be captured on a solid phase by contacting the substrate with a solid phase comprising groups capable of binding to said moieties; this contacting can be accomplished prior to, during, and/or after the sample is contacted with the enzyme sample. In a different embodiment, the substrate is non-specifically captured on a solid phase.

Classes of nucleic acid joining enzymes that can be measured include polymerase, enzymes that covalently join nucleic acid molecules including proteins involved with DNA recombination (e.g. integrases & recombinases), as well as DNA and RNA ligases.

An example of a format of the type mentioned herein is that of a strand transfer assay for the enzyme integrase. In this format, a viral-specific donor DNA sequence that comprises a biotin is attached to magnetic beads via a biotin-streptavidin interaction. This configuration allows one to pre-bind the donor with integrase and wash the unbound enzyme prior to the addition of target DNA linked to RuBpy. The integrase first randomly nicks the RuBpy-labeled target molecules. DNA strand transfer catalyzed by integrase leads to the formation of a covalent bond between the 3' end of the biotinylated donor molecule and the 5' end of the nicked RuBpy-labeled target molecule leading to an increase in the ECL signal from RuBpy on the magnetic beads, as measured using an ORIGEN analyzer.

C. Method for Assaying a Sample for an Enzyme Activity that Cleaves Nucleic Acids that Results in a Decrease in ECL Signal In an embodiment of the present invention, an enzyme of interest that cleaves nucleic acids (e.g., a nuclease, Dnase, Rnase, or restriction endonuclease) is measured in a sample by combining the sample with a predetermined (except in the case of an enzyme activity with random specificity) nucleic acid substrate capable of being cleaved by the enzyme of interest, wherein said substrate comprises one or more ECL labels (advantageously bipyridyl- or phenanthroline-containing complexes of Ru or Os, most advantageously RuBpy) and said substrate is linked to a solid phase (advantageously a magnetic bead or an electrode). The enzyme can be specific for a specific nucleic acid sequence or structure, or can have limited or no specificity. The nucleic acid substrate can be single stranded or double stranded or have regions of both. Advantageously, the nucleic acid substrate is 4-1000 kilobases in length, more advantageously 4-100 kilobases in length, and most advantageously 4-30 kilobases in length. The substrate is designed or prepared so that the enzymatic reaction decouples at least one ECL label on a substrate molecule (advantageously, all the ECL labels on the substrate) from the solid phase. The extent of enzymatic cleavage is determined by a measurement of the ECL labels remaining on the solid phase. Increased enzymatic activity leads to an increase in the decoupling of the ECL labels from the solid phase and, therefore, a decrease in ECL signal. Alternatively, the extent of enzymatic cleavage can be determined by a measurement of the ECL labels released from the solid phase into solution (e.g., the ECL from ECL labels in solution can be preferentially measured at an electrode in the presence of ECL labels present on particulate solid phases in suspension). In this alternative embodiment, increased enzymatic activity results in an increase in ECL signal.

These measurements of ECL labels are highly quantitative, sensitive, and precise. Advantageously the assay has a detection limit (for measuring a nucleic acid cleaving enzyme, its nucleic acid substrate, or an inhibitor of the enzyme) of less than 1 nmol, more advantageously, the detection limit is less than 1 pmol, even more advantageously, the detection limit is less than 1 fmol, even more advantageously, the detection limit is less than 1 amol.

Advantageously, the sample is contacted with the nucleic acid substrate for a defined period of time under defined conditions (e.g., temperature, pH, etc.) prior to the ECL measurement. In alternate embodiments, the protein or peptide substrate is not linked to a solid phase but comprises moieties that can be captured on a solid phase (e.g., biotin, specific nucleic acid sequences, or haptens); one of these embodiments in illustrated in FIG. 8. The substrate can be captured on a solid phase by contacting the substrate with a solid phase comprising groups capable of binding to said moieties; this contacting can be accomplished prior to, during, and/or after the sample is contacted with the enzyme sample. In a different embodiment, the substrate is non-specifically captured on a solid phase.

A protocol for an ECL-based assay for measuring the enzymatic cleavage of viral specific sequences by viral integrase is described in detail below. Integrase is a retroviral enzyme that possesses several distinct catalytic activities including those that promote processing and strand transfer functions. The processing activity functions to cleave the DNA copy of the retroviral genome in a sequence-specific fashion between the GA and CT bases of a GACT sequence. This activity is necessary for the integration of the viral DNA into the host genome. The assay measures the cleavage of a double stranded nucleic acid substrate (advantageously having a length of between 18-30 bases) comprising a GACT sequence on one of the 3' ends, a biotin on one end, and a RuBpy label on the other end.

The substrate (advantageously, at a concentration of between 0.1 and 200 uM) in a buffered solution (advantageously, at a pH of between 6.5-8.0 and containing a cation such as manganese or magnesium at a concentration of between 10-100 mM) is combined with the integrase sample and incubated (advantageously, at a temperature between 24-37° C. for between 5-1000 min.). Streptavidin-coated magnetic particles (advantagously, between 5-50 ug or Streptavidin DynaBeads) are then added and the suspension mixed for 10 min. The ECL from RuBpy remaining on the magnetic beads or released into solution is measured on an ORIGEN analyzer (IGEN International) running, respectively, in magnetic capture or solution phase modes. The integrase activity is directly related to the ECL from RuBpy released into solution and correlates with a drop in ECL from RuBpy on the magnetic beads.

D. Method for Assaying a Sample for the Presence of an Enzyme Activity that Cleaves Peptides or Proteins In another embodiment of the present invention, an enzyme of interest that cleaves peptides or proteins (e.g., a protease or a peptidase) is measured in a sample by combining the sample with a predetermined (except in the case of an enzyme activity with random specificity) protein or peptide substrate capable of being cleaved by the enzyme of interest, wherein said substrate comprises one or more ECL labels (advantageously, bipyridyl- or phenanthroline-containing complexes of Ru or Os, most advantageously RuBpy) and said substrate is linked to a solid phase (advantageously a magnetic bead or an electrode). The enzyme can be specific for a specific protein or peptide sequence or structure, or can have limited or no specificity. The substrate is designed or prepared so that the enzymatic reaction decouples at least one ECL label on a substrate molecule (advantageously all the ECL labels on the substrate) from the solid phase. Advantageously, the substrate is 4-1000 amino acids in length, more advantageously 4-100 amino acids in length, and most advantageously 4-40 amino acids in length. The extent of enzymatic cleavage is determined by a measurement of the ECL labels remaining on the solid phase. Increased enzymatic activity leads to an increase in the decoupling of the ECL labels from the solid phase and, therefore, a decrease in ECL signal. Alternatively, the extent of enzymatic cleavage can be determined by a measurement of the ECL labels released from the solid phase into solution (e.g., the ECL from ECL labels in solution can be preferentially measured at an electrode in the presence of ECL labels present on particulate solid phases kept in suspension). In this alternative embodiment, increased enzymatic activity results in an increase in ECL signal.

These measurements of ECL labels are highly quantitative, sensitive, and precise. Advantageously the assay has a detection limit (for measuring a protein cleaving enzyme, its substrate, or an inhibitor of the enzyme) of less than 1 nmol, more advantageously, the detection limit is less than 1 pmol, even more advantageously, the detection limit is less than 1 fmol, even more advantageously, the detection limit is less than 1 amol.

Advantageously, the sample is contacted with the protein or peptide substrate for a defined period of time under defined conditions (e.g., temperature, pH, etc.) prior to the ECL measurement. In alternate embodiments, the protein or peptide substrate is not linked to a solid phase but comprises moieties that can be captured on a solid phase (e.g., biotin, specific nucleic acid sequences, or haptens). The substrate can be captured on a solid phase by contacting the substrate with a solid phase comprising groups capable of binding to said moieties; this contacting can be accomplished prior to, during, and/or after the sample is contacted with the enzyme sample. In a different embodiment, the substrate is non-specifically captured on a solid phase.

E. Method for Assaying for the Presence of a Specific Nucleic Acid Sequence

In another embodiment of the present invention, a nucleic acid sequence of interest in a sample is measured by combining the sample with a predetermined (with respect to at least 10 nucleotides) nucleic acid probe (advantageously 8 to 10,000 nucleotides, more advantageously 15 to 1000 nucleotides) comprising a sequence complementary (or partially complementary) to the sequence of interest, said probe comprising an ECL label (advantageously a bipyridyl- or phenanthroline-containing complex of Ru or Os, most advantageously RuBpy) and a moiety capable of being captured on a solid phase (advantageously, biotin, a specific nucleic acid sequence, or a hapten). This combining is advantageously carried out in a buffer solution and a temperature (advantageously 0-100° C., most advantageously, 4-70° C. ) that promotes the specific hybridization of the sequence of interest with its complementary sequence. The sample is then incubated with a nucleic acid-cleaving enzyme specific for single-stranded nucleic acid molecules (e.g., RNase A, mung bean nuclease, or nuclease $S_1$). The resulting mixture is contacted with a solid phase capable of capturing said moiety and the captured ECL labels are measured by ECL (e.g., on an ORIGEN analyzer, IGEN International. The ECL signal increases with the amount of labeled nucleic acid hybridized to the sequence of interest and thus serves as a direct measure of the quantity of specific sequence found in the nucleic acid sample preparation. In an alternate embodiment, the ECL labeled probe is directly linked to a solid phase and the solid phase is present during the binding and cleavage reactions. In another alternate embodiment, a nuclease specific for double stranded nucleic acids is used (e.g., nuclease BAL 31 or exonuclease III); in this embodiment, specific hybridization leads to a decrease in ECL signal from ECL labels on the solid phase.

These measurements of ECL labels are highly quantitative, sensitive, and precise. Advantageously the assay has a detection limit (for measuring a nucleic acid sequence) of less than 1 nmol, more advantageously, the detection limit is less than 1 pmol, even more advantageously, the detection limit is less than 1 fmol, even more advantageously, the detection limit is less than 1 amol.

The following Examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1

A DNase Protection Assay for the Assessment of DNA-protein Interactions

This example illustrates the use of the invention to measure protein-DNA interactions, specifically, the binding of the transcription factor NFkβ with its consensus DNA sequence. A schematic depicting the assay format can be found in the detailed description of the invention. DNAse 1 and NFkβ were purchased from Promega Corp. A DNA substrate containing a consensus DNA sequence for NFk was prepared by Midland Certified Reagent Co. by solid phase synthesis. The sequence of the substrate is shown below. The nucleotides shown in brackets were linked by phosphorothioate linkages; the other linkages were standard phosphodiester bonds. One of the strands of the double stranded DNA substrate was labeled at the 5'-end with RuBpy and at the 3'-end with biotin using standard labeling techniques.

```
                                                   (SEQ ID NO:1)
5'-RuBpy-[AGTTGAGG]GGACTTT[CCCAGGC]-Biotin-3'

(SEQ ID NO:2)
            TCAACTCCCCTGAAAGGGTCCG-5'
```

The labeled DNA substrate (50 fmol), poly dI-dC (1 ug, to reduce non-specific protein-DNA interactions) and varying amounts of recombinant NFkβ (p50 subunit) were combined in a 20 uL volume and incubated for 30 min. at room temperature. Dnase 1 (2 Units in a volume of 2 uL, Promega Corp.) was then added and the incubation was continued for an additional 30 min. at room temperature. The reaction was terminated and the biotin-labeled DNA sequences captured by in the addition of 10 μg of streptavidin Dynabeads (IGEN, International) in 0.3 ml PBS-1 containing 0.2 M EDTA, followed by incubation for 15 minutes. The reaction mixture was introduced into an ORIGEN Analyzer (IGEN International) running in Magnetic Capture Mode and the ECL signal from RuBpy on the magnetic beads was determined in the presence of a solution containing tripropylamine (ORIGEN Assay Buffer, IGEN International). A control was also run in the absence of Dnase to determine the ECL signal obtained from the uncleaved substrate. Table I shows that the addition of Dnase to unprotected DNA gave a >20 fold reduction in signal. The addition of NFkβ gave a dose dependent increase in signal relative to that obtained from unprotected DNA, the magnitude of which approached, for high concentrations of NFkβ, the signal obtained in the absence of DNAse. The experiment was repeated with an DNA substrate with the same nucleotide sequence but containing only phosphodiester linkages and similar results were obtained.

TABLE I

| Dnase | NFkB (p50 subunit) | ECL Signal |
|---|---|---|
| 0 | 0 | 2591957 |
| 2 U | 0 | 96862 |

TABLE I-continued

| Dnase | NFkB (p50 subunit) | ECL Signal |
|---|---|---|
| 2 U | 7 ng | 1729305 |
| 2 U | 3.5 ng | 1383572 |
| 2 U | 1.75 ng | 709996 |
| 2 U | 0.87 ng | 425194 |

The specificity of the assay was determined by replacing the specific binding protein NFkβ with other DNA binding proteins specific for sequences not present on the DNA substrate (the phosphorothioate containing substrate was used). Table II shows only the specific binding protein, NFkβ, was able to confer nuclease protection to the DNA substrate containing the NFkβ consensus sequence. The DNA binding proteins AP-1, AP-2, and SP-1 showed no ability to protect against nuclease attack.

TABLE II

| Transcription Factor | DNase Added | ECL Signal |
|---|---|---|
| None | No | 2334309 |
| None | Yes | 54041 |
| NFkB | Yes | 1209953 |
| AP-1 | Yes | 32303 |
| AP-2 | Yes | 32289 |
| SP-1 | Yes | 38880 |

The DNAse protection assay was able to specifically detect the binding of the NFkβ consensus sequence to NFkβ present in nuclear extracts. We replaced the recombinant NFkβ used in the previous experiments with the NFkβ activity present in 1 uL of the nuclear extract from HeLa cells (Promega Corp.). Table III gives the specific ECL signal obtained from the assay (given as the difference between the ECL signal for the assay and the ECL signal measured for unprotected DNA) and shows that the nuclear extract was able to protect the DNA substrate from cleavage. The protection was due to a specific interaction between NFkβ and its consensus sequence. Table III also shows that a specific competitor of the interaction (a 100 fold excess of unlabeled DNA containing the NFkβ consensus sequence) reversed the protective effect of the cellular extract. In contrast, non specific sequences (100 fold excesses of unlabeled DNA containing the consensus sequences for AP-1 or SP-1) had no effect. The use of a DNA substrate having only phosphodiester bonds (i.e., no phophorothioate) gave similar specificity although the specific ECL signals were lower.

TABLE III

Determination of NFkβ Binding Activity in HeLa Cell Extract

| Competitor Sequence Used | Specific ECL Signal |
|---|---|
| None | 744155 |
| SP-1 | 665826 |
| AP-1 | 829931 |
| NFkB | 0 |

A similar experiment was conducted using a dual labeled SP-1 consensus whose sequence is given below.

(SEQ ID NO:3)
5'-Ruthenium-GATCGAACTGACCGCCCGCGGCCCGT-Biotin-3'

(SEQ ID NO:4)
CTAGCTTGACTGGCGGGCGCCGGGCA

Table IV not only show the ability to measure SP-1 binding activity in a complex protein preparation, but also demonstrates that only the specific competitor sequence was able to successfully compete in the binding reaction.

TABLE IV

Determination of SP-1 Binding Activity in HeLa Cell Extract

| Competitor Sequence Used | ECL Signal |
|---|---|
| None | 1385846 |
| SP-1 | 0 |
| AP-1 | 1172548 |
| NFkB | 1323636 |

Example 2

An ECL-based Assay for the Measurement of Protease Activity

This assay system consists of a ruthenylated (RuBpy-labeled) substrate immobilized on paramagnetic beads and the enzyme of interest. The RuBpy label is released by the action of the enzyme. The ECL of the free label is measured using the ORIGEN Analyzer (IGEN International).

Dynabead® M280 Sheep anti-mouse IgG coated beads (IGEN International, Inc.) were RuBpy-labeled at a 200:1 challenge ratio of RuBpy to IgG to introduce RuBpy groups on the immobilized IgG molecules. The labeling was carried out using a derivative of RuBpy linked to an NHS ester (TAG-NHS, IGEN International) according to established procedures. The beads were then washed three times, thirty minutes each, at 4° C. with equal volumes of PBS, pH 7.8, and once overnight at 4° C. Replicate test samples were prepared with 100 µl of solutions containing known amounts of Proteinase K (Sigma) in phosphate buffered saline, pH 7.8 and 25 µl of 1.2 mg/ml TAG labeled Sheep anti-mouse beads. The samples were shaken for 30 minutes at 37° C. The reaction was quenched by the addition of 1 mL of a solution containing tripropylamine (ORIGEN Assay Buffer, IGEN International, Inc.) and the protease activity was quantitated on the ORIGEN 1.5 Analyzer with the solution phase default settings (i.e., the beads are kept in suspension so as to preferentially measure ECL at the electrode from RuBpy groups in solution) except for high vortex speed. FIG. 9 shows the ECL signal as a function of the concentration of Proteinase K; the figure shows that the ECL signal is directly related to the concentration of enzyme.

Example III

An ECL-Based Assay for the Measurement of Factor Xa Activity

Factor Xa is a serine protease that cleaves the site adjacent to the arginine in the amino acid sequence IEGRX. The assay uses a peptide substrate that is labeled at the N-terminus with RuBpy and at a lysine at the carboxy terminus with biotin (RuBpy-IEGRGUEUEK-Biotin). Streptavidin-coated Dynabeads (IGEN International) were used to capture the labeled-peptide. The captured peptide is incubated with a sample containing the protease. Increasing amounts of protease in the sample led to increased rates of cleavage and (for a given amount of time) less RuBpy on the beads and more RuBpy in solution. The reaction products were analyzed on an ECL measurement instrument (ORIGEN Analyzer, IGEN International). The measurements were carried out in Solution Mode (i.e., the samples were analyzed under conditions that did not lead to significant settling of the bead suspension on the electrode; under these conditions the ECL signal was primarily due ECL labels released into solution and increased with increasing protease activity). The measurement can, alternatively, be carried out in Bead Capture Mode (i.e., a magnetic field is used to collect the magnetic beads are collected on the electrode surface; under these conditions, the ECL signal is primarily due to ECL labels on the solid phase and decreases with increased protease activity).

The protocol used was as follows: Factor Xa protease (1.28 Units in 5 uL) was combined with 20 uL of streptavidin Dynabeads (precoated with labeled substrate) and 175 uL of reaction buffer (50 mM tris, pH 8.0, 200 mM NaCl, 6 mM $CaCl_2$) and incubated at 37° C. for varying amounts of time. At the end of the predetermined incubation time, a 5 uL aliquot of the reaction mixture was combined with 345 uL of a tripropylamine containing buffer (ORIGEN Assay Buffer, IGEN International) and the mixture analyzed on an ORIGEN analyzer in Solution Mode. As a negative control, the experiments were repeated for the same times without protease. For an incubation time of 0 min. (i.e., the reaction was not allowed to occur), the measured ECL signal was approximately the same as the negative control. After 45 min. of incubation, the ratio of the ECL signal to that of the negative control was 4:1.

It will be readily apparent to those skilled in the art that numerous modifications and additions may be made to both the present invention, the disclosed device, and the related system without departing from the invention disclosed.

What is claimed is:

1. A method of assaying a sample for an enzyme activity that joins a first substrate with a second substrate to form a product or for a factor that affects the activity of said enzyme, wherein the presence, concentration, or activity of said enzyme or said factor is not known, comprising:

(a) forming a composition comprising said sample, said first substrate and said second substrate, said first substrate being linked to a luminescent label and said second substrate being linked to a capture moiety;

(b) incubating said composition under conditions wherein said enzyme can form said product at a differing rate in the presence or absence of said enzyme or factor, wherein said product is linked to said luminescent label and said capture moiety and wherein said enzyme or factor is not a part of the product;

(c) capturing said capture moiety on an electrode;

(d) applying voltage at said electrode so as to induce said luminescent label in said product to emit luminescence; and (e) measuring emitted luminescence so as to measure the presence of said enzyme or factor in said sample, wherein said enzyme is selected from the group consisting of nucleic acid polymerases, nucleic acid ligases, integrases, ribosomes, and trans-glutaminases.

2. The method of claim 1, wherein said enzyme catalyzes formation of a covalent bond between said first substrate and said second substrate.

3. The method of claim 1, wherein said first substrate or said second substrate comprises peptides.

4. The method of claim 1, wherein said first substrate or said second substrate comprises nucleic acids.

5. A method of assaying a sample for an enzyme that cleaves a substrate or for a factor that affects the activity of said enzyme, wherein the presence, concentration, or activity of said enzyme or said factor is not known, comprising:

(a) forming a composition comprising said sample and said substrate, wherein said substrate is linked to a luminescent label and to a solid phase, wherein said solid phase is not a graphitic nanotube;

(b) incubating said composition under conditions wherein said enzyme can cleave said substrate so as to cleave said luminescent label from said solid phase;

(c) immobilizing said solid phase on an electrode;

(d) applying a voltage at said electrode so as to induce said luminescent label linked to said substrate to emit luminescence; and (e) measuring emitted luminescence so as to measure the presence of said enzyme or factor in said sample.

6. The method of claim 5, wherein said enzyme cleaves a covalent bond.

7. The method of claim 5, wherein said substrate comprises a peptide.

8. The method of claim 5, wherein said substrate comprises a nucleic acid.

9. The method of claim 5, wherein said enzyme is selected from the group consisting of nucleases, proteases and glycosidases.

10. The method of claim 1, wherein said electrode comprises elemental carbon.

11. The method of claim 1, wherein said composition further comprises an inhibitor of said activity and the measurement of said activity is correlated to the amount or inhibitory ability of said inhibitor.

12. The method of claim 1, wherein said electrode consists essentially of a metal.

13. The method of claim 12, wherein said metal comprises gold or platinum.

14. The method of claim 1, wherein said factor is selected from the group consisting of an enzyme, an enzyme inhibitor, a denaturing compound, an enzyme activator, an enzyme deactivator, and a co-enzyme.

15. The method of claim 5, wherein said composition further comprises an inhibitor of said activity and the measurement of said activity is correlated to the amount or inhibitory ability of said inhibitor.

16. The method of claim 5, wherein said electrode consists essentially of a metal.

17. The method of claim 16, wherein the metal comprises gold or platinum.

18. The method of claim 5, wherein said factor is selected from the group consisting of an enzyme, an enzyme inhibitor, a denaturing compound, an enzyme activator, an enzyme deactivator, and a co-enzyme.

19. The method of claim 5, wherein said factor is an enzyme.

20. The method of claim 5, wherein said factor is an enzyme inhibitor.

21. The method of claim 5, wherein said factor is a denaturing compound.

22. The method of claim 5, wherein said factor is an enzyme activator.

23. The method of claim 5, wherein said factor is an enzyme deactivator.

24. The method of claim 5, wherein said factor is a co-enzyme.

25. The method of claim 1, wherein said factor is an enzyme.

26. The method of claim 1, wherein said factor is an enzyme inhibitor.

27. The method of claim 1, wherein said factor is a denaturing compound.

28. The method of claim 1, wherein said factor is an enzyme activator.

29. The method of claim 1, wherein said factor is an enzyme deactivator.

30. The method of claim 1, wherein said factor is a co-enzyme.

31. The method of claim 1, wherein said enzyme is selected from the group consisting of nucleic acid polymerases, nucleic acid ligases, integrases and ribosomes.

32. The method of claim 1, wherein said enzyme is a trans-glutaminase.

* * * * *

UNITED STATES PATENT AND TRADEMARK OFFICE
CERTIFICATE OF CORRECTION

| | | |
|---|---|---|
| PATENT NO. | : 7,439,017 B2 | Page 1 of 1 |
| APPLICATION NO. | : 09/976437 | |
| DATED | : October 21, 2008 | |
| INVENTOR(S) | : Jeffrey A. Heroux et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 261 days.

should read (*) Notice: Subject to any disclaimer, the term of this patent is extended or adjusted under 35 U.S.C. 154(b) by 572 days.

Signed and Sealed this

Twenty-seventh Day of April, 2010

David J. Kappos
*Director of the United States Patent and Trademark Office*

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<221> NAME/KEY: misc_difference
<222> LOCATION: (1)..(8)
<223> OTHER INFORMATION: Nucleotides are linked by phophorothioate
      linkages
```

```
<221> NAME/KEY: misc_difference
<222> LOCATION: (16)..(22)
<223> OTHER INFORMATION: Nucleotides are linked by phorothioate linkages
<221> NAME/KEY: misc_difference
<222> LOCATION: (1)
<223> OTHER INFORMATION: 5'-Labeled with ruthenium tris-bipyridyl
<221> NAME/KEY: misc_difference
<222> LOCATION: (22)
<223> OTHER INFORMATION: 3'-Labeled with biotin
<223> OTHER INFORMATION: Description of Artificial Sequence:  Artificial
      sequence containing a consensus sequence for human
      NFkB

<400> SEQUENCE: 1
agttgagggg actttcccag gc                                               22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:  Artificial
      sequence containing consensus sequence for human
      NFkB

<400> SEQUENCE: 2
gcctgggaaa gtcccctcaa ct                                               22

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:Artificial
      sequence containing consensus sequence for human
      SP-1
<221> NAME/KEY: misc_difference
<222> LOCATION: (1)
<223> OTHER INFORMATION: 5'-Labeled with ruthenium tris-bipyridiyl
<221> NAME/KEY: misc_difference
<222> LOCATION: (26)
<223> OTHER INFORMATION: 3'-Labeled with biotin

<400> SEQUENCE: 3
gatcgaactg accgcccgcg gcccgt                                           26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:  Artificial
      sequence containing consensus sequence for human
      SP-1

<400> SEQUENCE: 4
acgggccgcg ggcggtcagt tcgatc                                           26
```